US012735704B2

(12) United States Patent
Kang

(10) Patent No.: US 12,735,704 B2
(45) Date of Patent: Sep. 15, 2026

(54) ANTICANCER ADJUVANT AND PHARMACEUTICAL COMPOSITION FOR TREATING ANTICANCER-AGENT-RESISTANT CANCER, AND KIT COMPRISING SAME

(71) Applicant: DONG-A UNIVERSITY RESEARCH FOUNDATION FOR INDUSTRY-ACADEMY COOPERATION, Busan (KR)

(72) Inventor: Tae Hong Kang, Busan (KR)

(73) Assignee: DONG-A UNIVERSITY RESEARCH FOUNDATION FOR INDUSTRY-ACADEMY COOPERATION, Busan (KR)

( * ) Notice: Subject to any disclaimer, the term of this patent is extended or adjusted under 35 U.S.C. 154(b) by 834 days.

(21) Appl. No.: 17/965,460

(22) Filed: Oct. 13, 2022

(65) Prior Publication Data

US 2023/0080252 A1 Mar. 16, 2023

Related U.S. Application Data

(63) Continuation of application No. PCT/KR2021/000458, filed on Jan. 13, 2021.

(30) Foreign Application Priority Data

Apr. 13, 2020 (KR) ........................ 10-2020-0044834

(51) Int. Cl.

| | |
|---|---|
| ***C12N 15/113*** | (2010.01) |
| ***A61K 31/513*** | (2006.01) |
| ***A61K 31/7068*** | (2006.01) |
| ***A61K 31/713*** | (2006.01) |
| ***A61K 33/243*** | (2019.01) |
| ***C12Q 1/6886*** | (2018.01) |

(52) U.S. Cl.

CPC .......... *C12N 15/113* (2013.01); *A61K 31/513* (2013.01); *A61K 31/7068* (2013.01); *A61K 31/713* (2013.01); *A61K 33/243* (2019.01); *C12Q 1/6886* (2013.01); *C12N 2310/14* (2013.01); *C12N 2320/31* (2013.01); *C12Q 2600/158* (2013.01)

(58) Field of Classification Search

CPC .............. C12N 15/113; C12N 2320/31; C12Q 2600/158; A61P 35/00

See application file for complete search history.

(56) References Cited

FOREIGN PATENT DOCUMENTS

| | | | |
|---|---|---|---|
| KR | 10-1036207 | B1 | 5/2011 |
| WO | WO 2010/129746 | A2 | 11/2010 |

OTHER PUBLICATIONS

Ross et al (Ageing Res. Review, vol. 11, pp. 473-484 (2012)) (Year: 2012).*
Sanduya et al (Frontiers in Bioscience, vol. 17, pp. 174-188 (2012) (Year: 2012).*
Deng et al (Tissue and Cell, vol. 94, 102785, pp. 1-8 (2025)) (Year: 2025).*
Griseri et al (Human Molecular Genetics, vol. 20, No. 23, pp. 4556-4568 (2011)) (Year: 2011).*
Carrick et al (Archives of Biochem. And Biophys., vol. 462, pp. 278-285 (2007)) (Year: 2007).*
Brooks et al (Biochim. et Biophys. Acta, vol. 1829, pp. 666-670 (2013)) (Year: 2013).*
Brennan et al (Cancer Res., vol. 69, No. 12, pp. 5168-5176 (2009)) (Year: 2009).*
Suswam et al (J. Neurooncolo., vol. 113, pp. 195-205 (2013)) (Year: 2013).*
Bost et al (ACS Nano, vol. 15, pp. 13993-14021 (2021)) (Year: 2021).*
Damase et al (Frontiers in Bioengineering and Biotechnology, vol. 9, Article 628137, pp. 1-24 (2021)) (Year: 2021).*
Osborn et al (Nucleic Acid Therapeutics, vol. 28, No. 3, pp. 128-136 (2018)) (Year: 2018).*
Kobelt et al (Cancer Gene Therapy in Gene Therapy of Cancer: Methods and Protocols, Methods in Molecular Biology, vol. 2521, pp. 1-15 (Springer Nature 2022)) (Year: 2022).*
Roberts et al (Nature Rev., Drug Discovery, vol. 19, pp. 673-694 (2020)) (Year: 2020).*
International Search Report for PCT/KR2021/000458 mailed on Apr. 16, 2021.
Lee Tae-Hee et al., "Posttranscriptional control of the replication stress response via TTP-mediatedmRNA stabilization", Oncogene, vol. 39, Nr:16, pp. 3245-3257, Feb. 21, 2020 (DOI: http://dx.doi.org/10.1038/s41388-020-1220-9).
Lee Se-Ra et al., "Tristetraprolin activation by resveratrol inhibits the proliferation and metastasis of colorectal cancer cells", International journal of oncology, vol. 53, pp. 1269-1278, 2018 (DOI: http://dx.doi.org/10.3892/jo.2018.4453).
Ganesh Shanthi et al., "Combination of siRNA-directed Gene Silencing With Cisplatin Reverses Drug Resistance in Human Non-small Cell Lung Cancer", Molecular Therapy-Nucleic Acids, vol. 2, e110, pp. 1-11, 2013 (DOI: http://dx.doi.org/10.1038/mtna.2013.29).
Sooncheol Lee et al., "A post-transcriptional program of chemoresistance by AU-rich elements and TTP in quiescent leukemic cells", Genome Biology, vol. 21 (33), 2020.
Office action issued on Feb. 16, 2022 from Korean Patent Office in a counterpart Korean Patent Application No. 10-2020-0044834 (all the cited references are listed in this IDS.) (English translation is also submitted herewith.).

(Continued)

*Primary Examiner* — Jane J Zara

(74) *Attorney, Agent, or Firm* — The PL Group, PLLC

(57) ABSTRACT

An anticancer adjuvant for treating anticancer-agent-resistant cancer includes a tristetraprolin inhibitor. If resistance to DNA replication inhibitory anticancer agents is exhibited, a substance for inhibiting the activity of tristetraprolin can be included as an anticancer adjuvant so as to maximize the effects of an anticancer agent, and thus is usable in cancer treatment.

2 Claims, 28 Drawing Sheets

Specification includes a Sequence Listing.

(56) References Cited

OTHER PUBLICATIONS

Notice of Allowance issued on Sep. 7, 2022 from Korean Patent Office in a counterpart Korean Patent Application No. 10-2020-0044834 (all the cited references are listed in this IDS.) (English translation is also submitted herewith.).

* cited by examiner

FIG. 1A siCTRL siTTP 0 2 4 12 0 2 4 12 post-UV (h)

TTP p-CHK1

CHK1 p-p53 p53 p-CHK2

CHK2

γH2AX

H2AX

ATR

ATM

GAPDH

FIG. 1F siCTRL
siTTP
DMSO
2
6
DMSO
2
6
HU rel. (h)
TTP
p-CHK1
CHK1
ATR
GAPDH

FIG. 4A

| Mock | | | | | 2 h post-UV | | | | | |
|---|---|---|---|---|---|---|---|---|---|---|
| - | + | - | - | + | - | + | - | - | + | siTTP |
| - | - | + | - | - | - | - | + | - | - | siClaspin |
| - | - | - | + | + | - | - | - | + | + | Claspin |

TTP

Claspin p-CHK1

CHK1

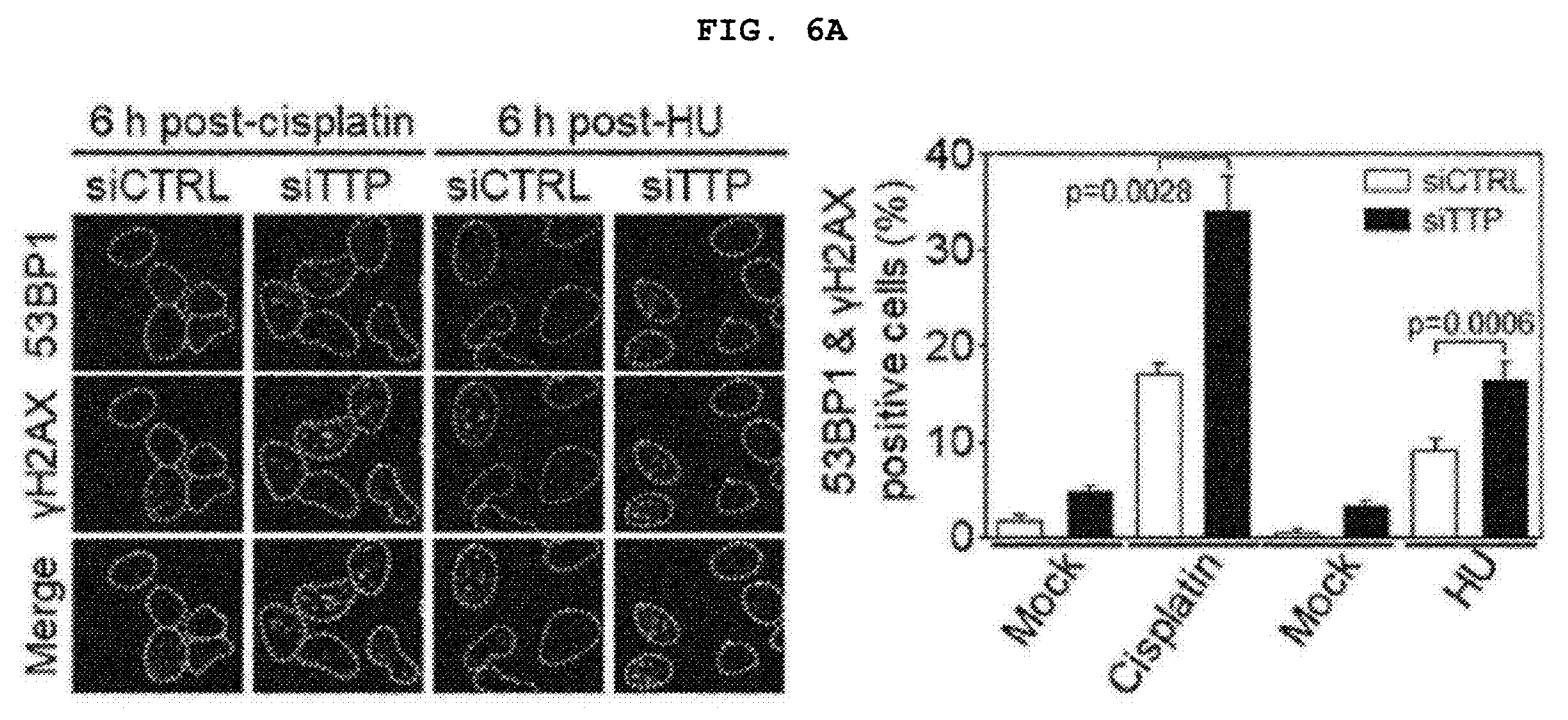

6 h post-cisplatin
siCTRL siTTP
6 h post-HU
siCTRL siTTP
53BP1
γH2AX
Merge

53BP1 & γH2AX positive cells (%)
0
10
20
30
40
siCTRL
siTTP
p=0.0028
p=0.0006
Mock
Cisplatin
Mock
HU

FIG. 6A

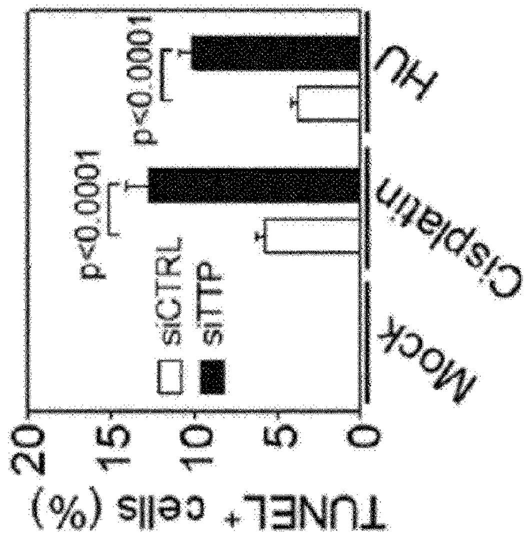
FIG. 6E
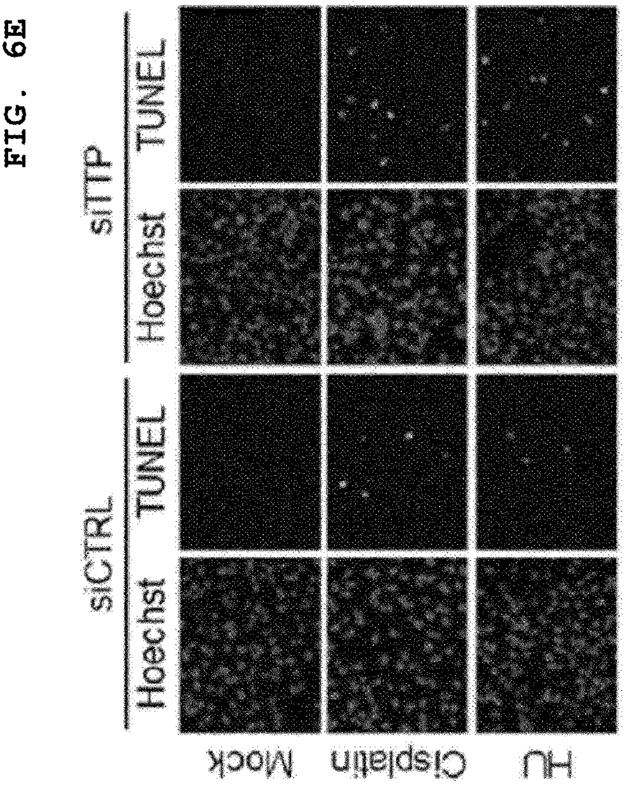

SEQUENCE LISTING

```
Sequence total quantity: 22
SEQ ID NO: 1            moltype = RNA  length = 25
FEATURE                 Location/Qualifiers
misc_feature            1..25
                        note = siTTP-892
source                  1..25
                        mol_type = other RNA
                        organism = synthetic construct
SEQUENCE: 1
atccgaccct gatgaatatg ccagc                                        25

SEQ ID NO: 2            moltype = RNA  length = 25
FEATURE                 Location/Qualifiers
misc_feature            1..25
                        note = siTTP-1209
source                  1..25
                        mol_type = other RNA
                        organism = synthetic construct
SEQUENCE: 2
ccccaagtgt gcaagctcag tattc                                        25

SEQ ID NO: 3            moltype = DNA  length = 21
FEATURE                 Location/Qualifiers
misc_feature            1..21
                        note = siCTRL
source                  1..21
                        mol_type = other DNA
                        organism = synthetic construct
SEQUENCE: 3
gcaagcatcg gctagtacgt a                                            21

SEQ ID NO: 4            moltype = DNA  length = 20
FEATURE                 Location/Qualifiers
misc_feature            1..20
                        note = TTP primer
source                  1..20
                        mol_type = other DNA
                        organism = synthetic construct
SEQUENCE: 4
tccacaaccc tagcgaagac                                              20

SEQ ID NO: 5            moltype = DNA  length = 20
FEATURE                 Location/Qualifiers
misc_feature            1..20
                        note = TTP primer
source                  1..20
                        mol_type = other DNA
                        organism = synthetic construct
SEQUENCE: 5
gacagtggga gacggaagag                                              20

SEQ ID NO: 6            moltype = DNA  length = 20
FEATURE                 Location/Qualifiers
misc_feature            1..20
                        note = Claspin primer
source                  1..20
                        mol_type = other DNA
                        organism = synthetic construct
SEQUENCE: 6
gtttgggttc agctcaggtg                                              20

SEQ ID NO: 7            moltype = DNA  length = 20
FEATURE                 Location/Qualifiers
misc_feature            1..20
                        note = Claspin primer
source                  1..20
                        mol_type = other DNA
                        organism = synthetic construct
SEQUENCE: 7
tcgtaggagg aaggagttgg                                              20

SEQ ID NO: 8            moltype = DNA  length = 23
FEATURE                 Location/Qualifiers
misc_feature            1..23
                        note = CHK1 primer
source                  1..23
                        mol_type = other DNA
                        organism = synthetic construct
```

-continued

```
SEQUENCE: 8
gcctgaaaga gacttgtgag aag                                            23

SEQ ID NO: 9           moltype = DNA  length = 24
FEATURE                Location/Qualifiers
misc_feature           1..24
                       note = CHK1 primer
source                 1..24
                       mol_type = other DNA
                       organism = synthetic construct
SEQUENCE: 9
aaggccgaaa gattcccact acct                                           24

SEQ ID NO: 10          moltype = DNA  length = 17
FEATURE                Location/Qualifiers
misc_feature           1..17
                       note = GAPDH primer
source                 1..17
                       mol_type = other DNA
                       organism = synthetic construct
SEQUENCE: 10
gtctcctctg acttcaa                                                   17

SEQ ID NO: 11          moltype = DNA  length = 17
FEATURE                Location/Qualifiers
misc_feature           1..17
                       note = GAPDH primer
source                 1..17
                       mol_type = other DNA
                       organism = synthetic construct
SEQUENCE: 11
accaccctgt tgctgta                                                   17

SEQ ID NO: 12          moltype = DNA  length = 20
FEATURE                Location/Qualifiers
misc_feature           1..20
                       note = ARE1
source                 1..20
                       mol_type = other DNA
                       organism = synthetic construct
SEQUENCE: 12
ggccactgat ttcaattctg                                                20

SEQ ID NO: 13          moltype = DNA  length = 20
FEATURE                Location/Qualifiers
misc_feature           1..20
                       note = ARE1
source                 1..20
                       mol_type = other DNA
                       organism = synthetic construct
SEQUENCE: 13
ggaggcagag attgtggtga                                                20

SEQ ID NO: 14          moltype = DNA  length = 20
FEATURE                Location/Qualifiers
misc_feature           1..20
                       note = ARE2
source                 1..20
                       mol_type = other DNA
                       organism = synthetic construct
SEQUENCE: 14
gacccttcct gggactgaat                                                20

SEQ ID NO: 15          moltype = DNA  length = 20
FEATURE                Location/Qualifiers
misc_feature           1..20
                       note = ARE2
source                 1..20
                       mol_type = other DNA
                       organism = synthetic construct
SEQUENCE: 15
ccatggtggc cttctctcaa                                                20

SEQ ID NO: 16          moltype = DNA  length = 20
FEATURE                Location/Qualifiers
misc_feature           1..20
                       note = ARE3
```

-continued

```
source                  1..20
                        mol_type = other DNA
                        organism = synthetic construct
SEQUENCE: 16
ttgagagaag gccaccatgg                                                20

SEQ ID NO: 17           moltype = DNA  length = 20
FEATURE                 Location/Qualifiers
misc_feature            1..20
                        note = ARE3
source                  1..20
                        mol_type = other DNA
                        organism = synthetic construct
SEQUENCE: 17
gcacactctc ttccaactgc                                                20

SEQ ID NO: 18           moltype = DNA  length = 20
FEATURE                 Location/Qualifiers
misc_feature            1..20
                        note = ARE4
source                  1..20
                        mol_type = other DNA
                        organism = synthetic construct
SEQUENCE: 18
cagagccagc ctatgtctca                                                20

SEQ ID NO: 19           moltype = DNA  length = 21
FEATURE                 Location/Qualifiers
misc_feature            1..21
                        note = ARE4
source                  1..21
                        mol_type = other DNA
                        organism = synthetic construct
SEQUENCE: 19
acagagccag cctatgtctc a                                              21

SEQ ID NO: 20           moltype = RNA  length = 25
FEATURE                 Location/Qualifiers
misc_feature            1..25
                        note = siClaspin-494
source                  1..25
                        mol_type = other RNA
                        organism = synthetic construct
SEQUENCE: 20
aaccttgctt agagctgagt cttca                                          25

SEQ ID NO: 21           moltype = DNA  length = 20
FEATURE                 Location/Qualifiers
source                  1..20
                        mol_type = genomic DNA
                        organism = Homo sapiens
SEQUENCE: 21
caattctgca gtatttacaa                                                20

SEQ ID NO: 22           moltype = DNA  length = 20
FEATURE                 Location/Qualifiers
misc_feature            1..20
                        note = mutated claspin
source                  1..20
                        mol_type = other DNA
                        organism = synthetic construct
SEQUENCE: 22
caattctgca gtatctacaa                                                20
```

ANTICANCER ADJUVANT AND PHARMACEUTICAL COMPOSITION FOR TREATING ANTICANCER-AGENT-RESISTANT CANCER, AND KIT COMPRISING SAME

CROSS-REFERENCE TO RELATED APPLICATION AND CLAIM OF PRIORITY

The present application is a continuation of application to International Application No. PCT/KR2021/000458 with an international filing date of Jan. 13, 2021, which claims the benefit of Korean Patent Application No. 10-2020-0044834 filed on Apr. 13, 2020 at the Korean Intellectual Property Office, the disclosures of which are incorporated by reference herein in their entirety.

BACKGROUND

1. Technical Field

The present invention relates to an anticancer adjuvant and pharmaceutical composition for treating anticancer-agent-resistant cancer, and kit comprising the same.

2. Background Art

Genomic instability is a key driving force of cancer that can arise owing to defects in the DNA damage response or increased replication stress. Replication stress can be defined as the slowing or stalling of replication fork progression or DNA synthesis, and usually results in the formation of stretches of single-stranded DNA (ssDNA). The persistence of ssDNA that is coated by the ssDNA-binding protein RPA (replication protein A) then generates a signal platform for activation of the ATR (ataxia-telangiectasia mutated and Rad3-related) kinase.

To sustain the integrity of stalled replication fork structures, ATR inhibits cell cycle progression by phosphorylating and activating CHK1. The ATR-CHK1 pathway then reduces replication fork speed and suppresses new origin firing to provide cells additional time to resolve stress and restart DNA synthesis. Extensive studies have firmly established the functions of the ATR-CHK1 pathway in the detection, stabilization, and restart of the stalled replication fork. Nonetheless, the regulation of ATR-CHK1 activity and the factors impinging on ATR-CHK1 regulation are still being elucidated.

Claspin is an essential factor for ATR-mediated CHK1 activation, which mediates the physical interaction between CHK1 and ATR on the RPA-coated ssDNA upon fork stalling or DNA resection. Besides, Claspin is necessary for efficient replication fork progression during the unperturbed S phase as it is an intrinsic component of the replisome and interacts with multiple core replisome components including DNA polymerases, MCM helicases, and CDC45. Indeed, depletion of Claspin causes a substantial reduction in normal replication fork velocity and a dramatic increase in the number of stalled replication forks, which ultimately leads to the embryonic lethality of the Claspin knockout mouse. While the cell cycle-dependent regulation of the Claspin expression has been relatively well documented, the regulation of Claspin levels under replication stress has not been reported yet.

Protein turnover via ubiquitin-mediated degradation during the cell cycle progression has been demonstrated to be one of the major mechanisms regulating Claspin expression. However, little is known about the transcriptional or post-transcriptional control of Claspin or the other key checkpoint factors involved in the replication stress response (RSR).

Posttranscriptional regulation of messenger RNA (mRNA) stability is essential for the cell to promptly respond to intracellular and extracellular stimuli. Tristetraprolin (TTP or ZFP36) is a tandem CCCH zinc finger protein that can bind directly to a cis-acting adenosine-and-uridine-rich element (ARE) within the 3'-untranslated region (3'UTR) of its target mRNAs. TTP then normally promotes the decay of these mRNAs by recruiting exosome complex for rapid shortening of the poly(A) tail but to fewer occasions, it may also increase the stability and translation of target mRNAs. TTP-deficient mice develop a complex inflammatory syndrome of arthritis, dermatitis, cachexia, autoimmunity, and myeloid hyperplasia due to the sustained upregulation of pro-inflammatory cytokine TNF-$\alpha$ in the absence of TTP. As a member of the family of immediate early response genes, TTP is induced by various stimuli, e.g., by mitogens in quiescent fibroblasts.

Recent studies indicate that TTP is also rapidly induced in response to doxorubicin treatment in a p53-dependent manner. By contrast, the potential roles of TTP in cancer cells during the DNA damage response have not been determined yet. Here, we report a crucial function of TTP during the RSR. DNA damage-induced TTP expression was necessary for the stabilization of Claspin mRNA, which is a prerequisite for ATR-CHK1 activation to maintain genome stability. Our study presents a novel regulatory mechanism of the ATR-CHK1 pathway by which TTP controls the Claspin mRNA stability in a posttranscriptional manner.

SUMMARY

An object of the present invention is to provide an anticancer adjuvant for treating cancer that is resistant to DNA replication inhibitory anticancer agents, and a pharmaceutical composition including the same.

In addition, another object of the present invention is to provide a composition for diagnosing resistance to DNA replication inhibitory anticancer agents and a kit including the same.

Further, another object of the present invention is to provide an information providing method for diagnosing resistance to DNA replication inhibitory anticancer agents.

1. An anticancer adjuvant for DNA replication inhibitory anticancer agent-resistant cancer, including a tristetraprolin inhibitor.

2. The anticancer adjuvant according to the above 1, wherein the tristetraprolin inhibitor is an siRNA represented by SEQ ID NO: 1 or SEQ ID NO: 2.

3. The anticancer adjuvant according to the above 1, wherein the DNA replication inhibitory anticancer agent is 5-fluorouracil, gemcitabine or cisplatin.

4. The anticancer adjuvant according to the above 1, wherein the cancer is lung cancer or colorectal cancer.

5. The anticancer adjuvant according to the above 1, wherein the anticancer adjuvant is for administration in combination with a DNA replication inhibitory anticancer agent.

6. A pharmaceutical composition for treating DNA replication inhibitory anticancer agent-resistant cancer, including a tristetraprolin inhibitor and a DNA replication inhibitory anticancer agent.

7. The pharmaceutical composition according to the above 6, wherein the tristetraprolin inhibitor is an siRNA represented by SEQ ID NO: 1 or SEQ ID NO: 2.

8. The pharmaceutical composition according to the above 6, wherein the DNA replication inhibitory anticancer agent is 5-fluorouracil, gemcitabine or cisplatin.

9. The pharmaceutical composition according to the above 6, wherein the cancer is lung cancer or colorectal cancer.

10. A composition for diagnosing resistance to DNA replication inhibitory anticancer agents, including a material that is specifically bound to tristetraprolin gene or a protein thereof.

11. The composition according to the above 10, wherein the material includes a primer set consisting of SEQ ID NOs: 4 and 5.

12. The composition according to the above 10, wherein the anticancer agent is at least one selected from the group consisting of 5-fluorouracil, gemcitabine or cisplatin.

13. A kit for diagnosing resistance to DNA replication inhibitory anticancer agents, including the composition according to any one of the above 10 to 12.

14. A method for providing information on diagnosis of resistance to DNA replication inhibitory anticancer agents, including: measuring an expression level of tristetraprolin gene or a protein thereof in a sample isolated from a diagnostic subject.

15. The method according to the above 14, wherein the diagnostic subject is a lung cancer or colorectal cancer patient.

16. The method according to the above 14, wherein the sample is selected from the group consisting of tissue, cells, blood, serum, plasma, saliva or urine.

17. The method according to the above 14, wherein the anticancer agent is at least one selected from the group consisting of 5-fluorouracil, gemcitabine or cisplatin.

18. The method according to the above 14, wherein, when the measured expression level is higher than that of a control, it is determined that the diagnostic subject has higher resistance to the DNA replication inhibitory anticancer agents than the control.

The anticancer adjuvant including the tristetraprolin inhibitor of the present invention may be used to treat cancer patients who have developed resistance to an anticancer agent in a patient group using DNA replication inhibitory anticancer agents, thereby maximizing anticancer therapeutic effects.

The pharmaceutical composition including: a tristetraprolin inhibitor; and a DNA replication inhibitory anticancer agent may be used in the treatment of cancer patients having developed resistance to anticancer agents in a patient group using DNA replication inhibitory anticancer agents thus to maximize anticancer therapeutic effects.

The composition, kit and method for diagnosing resistance to DNA replication inhibitory anticancer agents according to the present invention may effectively predict the therapeutic reactivity of anticancer agents, and enable selective, individual anticancer agent treatment for cancer patients.

BRIEF DESCRIPTION OF THE DRAWINGS

Figure 1A:
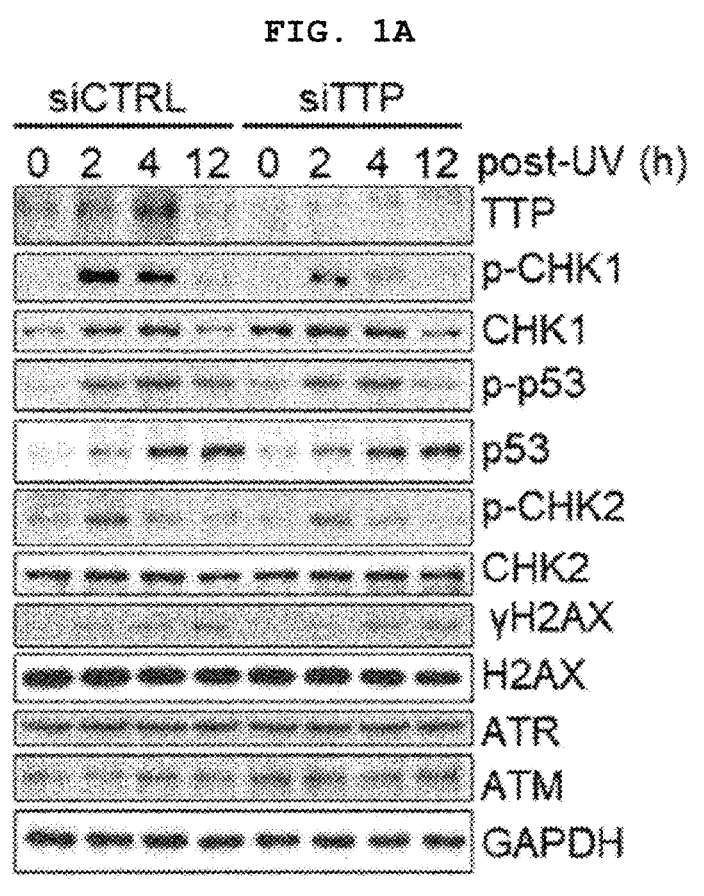

FIGS. 1A to 1F correspond to Example 1, and FIG. 1A shows the result of the immunoblot analysis with the indicated antibodies after 20 J/m$^2$ UV-C treatment of A549 (human lung carcinoma) cells transfected with the siCTRL and siTTP. FIG. 1B shows the result of the immunoblot analysis with the indicated antibodies after 20 J/m$^2$ UV-C treatment of A549 cells transfected with the vector expressing siRNA-resistant TTP. FIG. 1C shows the result of the immunostain of control or UV-treated cells with the indicated antibodies, and the nuclei stained with Hoechst 33342 are depicted as dotted circles. FIG. 1D is a quantification of the percentage of p-CHK1-positive cells from UV-treated data of FIG. 1C. FIG. 1E shows cells treated with the indicated inhibitors after UV irradiation, fixed for 2 hours, and then immunostained with an anti-p-CHK1 antibody. In each experiment, >100 cells were randomly chosen to determine the percentage of p-CHK1-positive cells. FIG. 1F shows the results of immunoblotting by treating either siCTRL—(control, 10 nM control siRNA) or siTTP transfected cells with DMSO or 4 mM HU for 2 hours, and then releasing them for the indicated periods.

FIG. 2A shows that either siCTRL- or siTTP-transfected A549 (human lung carcinoma) cells were sequentially pulse-labeled with IdU (red) for 20 min and CldU (green) for 40 min with or without UV-C (20 J/m2) exposure between the labeling procedures and were subjected to DNA fiber analysis. The ratios of CldU to IdU were calculated from active replication forks. FIG. 2B shows that A549 cells transfected with siCTRL, siTTP or a combination of siTTP and the vector expressing siRNA-resistant TTP, were pulse labeled with IdU, treated with 4 mM HU for 2 h, and release from HU block in presence of CldU for 6 h. Single-strand DNA (ssDNA; blue) was labelled with ssDNA-specific antibodies. Percentages of stalled forks were calculated by dividing the number of red-only tracts (stalled forks) by the total number of red-only plus red-green tracts (stalled and restarted forks, respectively). Analyses were performed on a minimum of 200 individual DNA fibers. FIG. 2C shows that A549 cells transfected with siCTRL, siTTP or a combination of siTTP and the vector expressing siRNA-resistant TTP were treated with 4 mM HU for 2 h, released for the indicated periods, and were pulse-labeled with EdU for the last 1 h. The recovery of S phase progression is presented as a percentage of EdU positive cells at 6 h after the release from HU treatment. In each experiment, >100 cells were randomly chosen to determine the percentage of EdU-positive cells. FIG. 2D shows that A549 cells transfected with either siCTRL or siTTP were sequentially pulse-labeled with IdU and CldU, followed by treatment with 4 mM HU for 6 h and then were subjected to DNA fiber analysis. The ratio of CldU to IdU in terms of length was calculated from active replication forks (red-green). The median value of over 200 fibers per experimental condition is indicated as bars. Statistical analysis was conducted using Mann-Whitney test.

FIG. 3A shows the result of quantitative real-time PCR (qRT-PCR) of the mRNA levels for indicated genes of A549 (human lung carcinoma) cells transfected with either siCTRL or siTTP treated without actinomycin D. FIG. 3B shows the result of qRT-PCR of the mRNA levels for indicated genes of A549 cells transfected with either the empty vector or the vector expressing siRNA-resistant TTP treated with actinomycin D for the indicated times. FIG. 3C shows the result of the RNA immunoprecipitation analysis performed with the antibody against TTP on the lysates of A549 cells transfected with either the empty vector or TTP-expressing vector with or without UV irradiation. The presence of TTP-binding sites in the 3'UTR of Claspin mRNA was analyzed by RT-PCR. GAPDH mRNA served as a negative control. FIG. 3D shows the result of the luciferase reporter assays of A549 cells cotransfected with psiCHECK2 luciferase reporter constructs (encoding mRNA containing either ARE1WT or ARE1Mut) and either the TTP-expressing vector or siTTP. Luciferase reporter activity was measured as the ratio of firefly luciferase signals to Renilla luciferase signals. FIG. 3E shows the result of immunoblot analysis with the indicated antibodies of whole-cell lysates of A549 cells which were cotransfected with either siCTRL or siTTP and either the empty vector or vector expressing siRNA-resistant TTP. A549 cells were treated with mock or 20 J/$m^2$ UV-C.

FIGS. 4A to 4C correspond to Example 3, and FIG. 4A shows the result of the immunoblot analysis with the indicated antibodies after mock or 20 J/$m^2$ UV-C treatment of A549 (human lung carcinoma) cells transfected with the indicated siRNAs, or the vector expressing siRNA-resistant Claspin. FIG. 4B shows the result of DNA fiber analysis of either siTTP- or siClaspin-transfected cells sequentially pulse-labeled with IdU(red) for 20 min and CldU (green) for 40 min with or without UV-C (20 J/$m^2$) exposure between the labeling procedures. The length ratio of CIdU to IdU was calculated from the active replication bifurcation (red-green, n>100). FIG. 4C shows the result of DNA fiber analysis after treatment with 4 mM HU for 6 h of A549 cells transfected with the indicated siRNAs or the vector expressing siRNA-resistant Claspin sequentially pulse labeled with IdU and CldU. The ratio of CldU to IdU in terms of length was calculated from active replication forks (red-green). The median value of over 200 fibers per experimental condition is indicated as bars. Statistical analysis was conducted using Mann-Whitney test.

FIG. 5A shows the representative images of the replicating tracts from indicated cells. FIG. 5B shows the median value of over 150 fibers per experimental condition indicated as bars. Statistical analysis was conducted using Mann-Whitney test.

FIGS. 6A to 6E correspond to Example 5, and FIG. 6A shows the result of the immunostaining with the indicated antibodies of either siCTRL- or siTTP-transfected A549 (human lung carcinoma) cells treated with either 4 mM HU or 10 μM cisplatin. In each experiment, >100 cells were randomly chosen to quantify the colocalization of 53BP1 and γH2AX foci. FIG. 6B show the result of the comet assay. The comet assay uncovered increased numbers of DNA breaks in TTP-deficient cells. Either siCTRL or siTTP-transfected A549 cells were treated with either 4 mM HU or 10 μM cisplatin. After drug removal, the extent of DNA breaks was assessed in a comet assay during alkaline electrophoresis. FIG. 6C shows the analysis of chromosomal aberrations in HCT116 (human colorectal carcinoma) cells after replication stress was applied. Either siCTRL- or siTTP-transfected cells were treated with either 4 mM HU or 20 μM cisplatin and then incubated with 0.1 μg/ml colcemid. Representative images illustrate Giemsa-stained metaphase spreads and the arrows indicate abnormal chromosomes. In total, 100 metaphases were scored for each experiment. FIG. 6D shows the result of the detection of apoptotic cells by immunofluorescence staining of cleaved caspase 3, an apoptosis factor. A549 cells were grown on coverslips and transfected with either siCTRL or siTTP. After 48 h, the cells were treated with either 4 mM HU or 20 μM cisplatin and allowed to recover for 24 h before fixation, followed by immunostaining of cleaved caspase 3. In each experiment, >100 cells were randomly chosen to determine the percentage of cleaved-caspase-3-positive cells. FIG. 6E shows the TUNEL assay. The TUNEL assay shows fluorescent labeling of apoptotic (TUNEL, green) versus all nuclei (Hoechst 33342, blue) among A549 cells after replication stress was applied. Either siCTRL- or siTTP-transfected cells were treated with either 4 mM HU or 20 μM cisplatin, and the TUNEL assay was performed. In each experiment, >200 cells were randomly chosen to determine the percentage of TUNEL-positive cells.

DETAILED DESCRIPTION

Figure 1B:
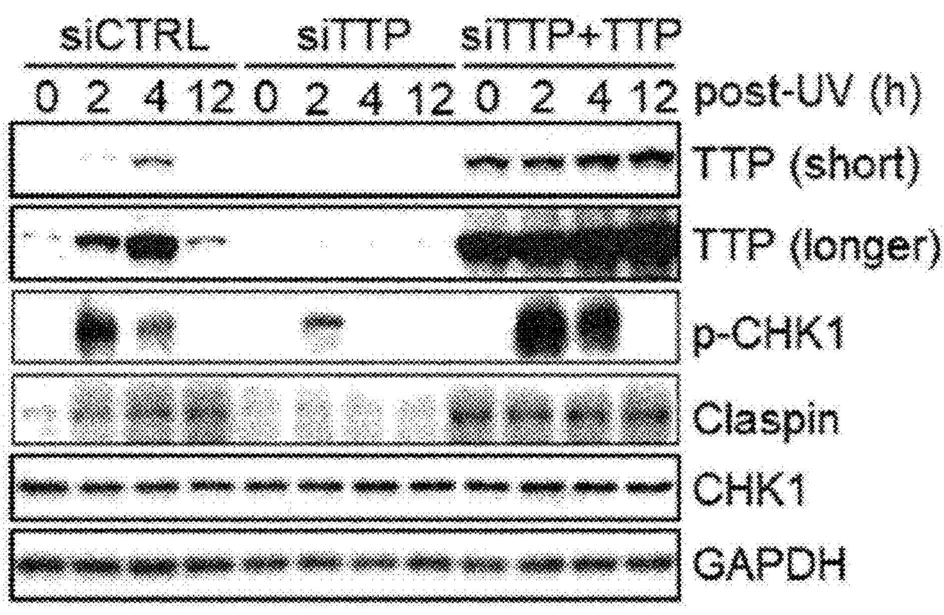

Hereinafter, the present invention will be described in detail.

The present invention relates to an anticancer adjuvant for DNA replication inhibitory anticancer agent-resistant cancer, which includes a tristetraprolin (TTP) inhibitor.

The tristetraprolin inhibitor is a substance capable of inhibiting the expression or activity of tristetraprolin.

Tristetraprolin selectively modulates ATR-CHK1 activity in response to DNA damage, and TTP is required for the ATR-CHK1 function in slowing down the replication fork speed in response to replication stress, and to restart replication fork while maintaining replication fork stability. Further, the activity of ATR-CHK1 may be regulated through post-transcriptional regulation of Claspin mRNA, wherein TTP is directly bound to Claspin ARE1 to maintain the stabilization of Claspin mRNA. TTP may also regulate the replication fork speed depending on Claspin.

The ATR-CHK1 pathway plays an important role in the replication stress response. When the ATR-CHK1 pathway is activated, it helps cells to survive from the stress and faithfully complete DNA replication. And ATR-CHK1 pathway is also implicated for the restart of stalled replication forks after the damage is tolerated or removed by repair systems.

The DNA replication inhibitory anticancer agent exhibits anticancer effects by preventing cancer cells from replicating DNA, and shows anticancer effects by increasing DNA replication stress of cancer cells. In the present invention, the anticancer agent may be 5-fluorouracil (5-FU), gemcitabine, cisplatin or the like.

The DNA replication inhibitory anticancer agent-resistant cancer in the present invention may mean any cancer involving anticancer agent resistance such that it exhibits a decrease in therapeutic effects or occurrence of side effects even if the treatment is maintained at the existing dose, when the DNA replication inhibitory anticancer agent is continuously used in a patient group using the DNA replication inhibitory anticancer agent. Specifically, cancer cell apoptosis effects occur only when the DNA replication stress on the cancer cells is not resolved. However, when anticancer agent resistance occurs as described above, the replication stress is not maximized compared to before, instead, is partially resolved thus to reduce therapeutic effects of the anticancer agent.

The anticancer adjuvant of the present invention is capable of inhibiting the expression or activity of tristetraprolin by including the tristetraprolin inhibitor, and does not show anticancer activity by itself. However, when used along with an anticancer agent, it may aid or improve the replication inhibitory effects by the anticancer agent. As described above, if the anticancer agent is continuously used, resistance to the anticancer agent may develop and thus the expected DNA replication inhibitory effects of cancer cells may not be sufficiently exerted. In such a case, by suppressing the expression or activity of tristetraprolin to maximize the replication stress, effects of inhibiting DNA replication of anticancer agents and the replication stress by the anticancer adjuvant may be increased, and thereby exhibiting anticancer effects to inhibit the replication of cancer cell DNA.

Types of the tristetraprolin inhibitor are not limited as long as they inhibit the activity or expression of tristetraprolin, and may be, for example, siRNA. It may have, for example, the sequence of SEQ ID NO: 1 or 2. In addition, short interfering RNA (shRNA), microRNA (miRNA), guide RNA (gRNA) or antisense oligonucleotide (ASO), which inhibit the activity of a target gene through complementary binding to the DNA or mRNA of the target gene, like siRNA, can also be used as tristetraprolin inhibitors.

With regard to the anticancer adjuvant for DNA replication inhibitory anticancer agent-resistant cancer according to the present invention, the cancer capable of exhibiting the resistance may be a solid cancer, preferably selected from the group consisting of lung cancer, ovarian cancer, colorectal cancer, colon cancer, pancreatic cancer, liver cancer, cervical cancer, kidney cancer, gastric cancer, prostate cancer, breast cancer, brain tumor, uterine cancer and bladder cancer, and more preferably selected from the group consisting of colorectal cancer and lung cancer.

The anticancer adjuvant of the present invention may be administered in combination with a DNA replication inhibitory anticancer agent. When administered in combination with an anticancer agent, the order of administration is not particularly limited, and the anticancer adjuvant of the present invention may be administered simultaneously or sequentially with the anticancer agent.

The present invention relates to a pharmaceutical composition for treatment of cancer that is resistant to DNA replication inhibitory anticancer agents, which includes a tristetraprolin inhibitor.

The pharmaceutical composition of the present invention may consist of an inhibitor to suppress tristetraprolin and the DNA replication inhibitory anticancer agent, but it is not limited thereto. The tristetraprolin inhibitor may inhibit expression or activity of tristetraprolin.

The tristetraprolin inhibitor may be used as described above, but it is not limited thereto.

The anticancer agent used herein may be any of the above-described types, but it is not limited thereto.

The type of cancer expressing the above-described resistance is as described above, but it is not limited thereto.

The anticancer adjuvant of the present invention may be prepared as a pharmaceutical preparation, and the pharmaceutical preparation may be prepared in the form of a unit dose through formulation using at least one selected from the group consisting of a pharmaceutically acceptable carrier, diluents and excipients, or may be prepared by introducing the adjuvant into a multi-dose container. In this case, the formulation may be in the form of a solution, suspension or emulsion in oil or aqueous medium, or may be in the form of an extract, powder, granule, tablet or capsule. The formulation may further include a dispersing agent or a stabilizing agent.

If necessary, the pharmaceutical preparation may further include a pharmaceutically acceptable carrier. The pharmaceutically acceptable carrier is commonly used in the process of formulation, and may include, for example, lactose, dextrose, sucrose, sorbitol, mannitol, starch, acacia gum, calcium phosphate, alginate, gelatin, calcium silicate, fine crystalline cellulose, polyvinylpyrrolidone, cellulose, water, syrup, methyl cellulose, methylhydroxybenzoate, propylhydroxybenzoate, talc, magnesium stearate and mineral oil, but it is not limited thereto.

The administration route of the anticancer adjuvant may include any general route as long as it can reach target tissues. According to the purposes, the administration may include intraperitoneal, intravenous, intramuscular, subcutaneous, intradermal, oral, intranasal, intrapulmonary, or rectal administration, but it is not limited thereto. Further, the anticancer adjuvant may be administered by any device capable of delivering an active substance to target cells.

The dosage of the anticancer adjuvant may be determined according to factors including, for example, type and severity of a disease, age and sex of a patient to which the adjuvant is administered, level of resistance to drugs, administration time, administration route and excretion rate, treatment period and concurrent drugs, and other factors well known in the medical field, and can be easily determined by those skilled in the art in consideration of all of the above factors. For example, the dosage may be about 0.0001 to 100 mg/kg, and preferably 0.001 to 10 mg/kg, and if necessary, the dosage may be divided into several times and administered at a regular time interval.

The pharmaceutical composition of the present invention may include 0.001 to 99.9% by weight ("wt. %"), specifically 0.1 to 99 wt. %, and more specifically 1 to 50 wt. % of the tristetraprolin inhibitor and the DNA replication inhibitory anticancer agent, based on a total weight of the composition.

The pharmaceutical composition may include a tristetraprolin inhibitor and a DNA replication inhibitory anticancer agent in the method exemplified above, and may be formulated and used in the form of oral formulation such as powder, granule, tablet, capsule, suspension, emulsion, syrup, aerosol, etc., an external preparation, a suppository, and a sterilized injection solution type formulation according to conventional methods, respectively, but it is not limited thereto.

The carrier, excipient and diluent that can be contained in the pharmaceutical composition may include lactose, dextrose, sucrose, dextrin, maltodextrin, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil, but they are not limited thereto. When formulating the composition, the formulation may be prepared using a diluent or excipient such as a filler, an extender, a binder, a wetting agent, a disintegrant and a surfactant, which are usually used in the art, but it is not limited thereto.

Solid preparations for oral administration may include tablets, pills, powders, granules, capsules, etc., but they are not limited thereto. Such solid preparations may be prepared by admixing the above-described compound with at least one or more excipients such as starch, calcium carbonate, sucrose or lactose, gelatin, etc. Further, other than simple excipients, lubricants such as magnesium stearate, talc, etc. may also be used.

Liquid formulations for oral use may include suspending agents, oral liquids, emulsions, syrup and the like. Other than simple diluents commonly used in the art such as water and liquid paraffin, various excipients such as wetting agents, sweeteners, fragrances, preservatives, etc. may be used. Formulations for parenteral administration may include sterile aqueous solution, non-aqueous solvent, suspending agents, emulsions, freeze-dried preparations, suppositories and the like. The non-aqueous solvents or suspending agents used herein may include propylene glycol, polyethylene glycol, vegetable oil such as olive oil, injectable ester such as ethyl oleate, etc. As a base of the suppository, witepsol, macrogol, tween 60, cacao butter, laurin, glycerogelatin, and the like may be used.

The preferred dosage of the pharmaceutical composition of the present invention varies depending on the patient's condition, body weight, severity of disease, drug form, administration route, and administration period, but may be appropriately selected by those skilled in the art. Specifically, the composition may be administered at 1 μg/kg to 400 mg/kg per day, and more specifically, at 1 mg/kg to 200 mg/kg. However, the scope of the present invention is not limited by the dosage.

The present invention provides a composition for diagnosing DNA replication inhibitory anticancer agent resistance, including a material that is specifically bound to a tristetraprolin gene or a protein thereof.

The material is not limited as long as it can detect TTP mRNA or a protein thereof.

The material may include a primer set consisting of SEQ ID NOs: 4 and 5. However, the sequence is not limited thereto, and the type thereof is not limited as long as it is a material capable of measuring the expression of the TTP gene.

In the present invention, the "primer" refers to a short gene sequence serving as a starting point of DNA synthesis, which is an oligonucleotide synthesized for use in diagnosis, DNA sequencing, etc. The primers may be synthesized and used with a length of typically 15 to 30 base pairs, but may vary depending on the purpose of use, and may be modified by methylation, capping, etc. by known methods.

The material may be one selected from the group consisting of antibodies, aptamers, DNA, proteins, and polypeptides.

In the present invention, the "antibody" refers to a protein molecule specific to an antigenic site. For the purposes of the present invention, the antibody refers to an antibody that is specifically bound to the marker protein, that is, NMI, and may include all of monoclonal antibodies, polyclonal antibodies, and recombinant antibodies.

The monoclonal antibody may be prepared using a hybridoma method well known in the art or a phage antibody library technology, but it may not be limited thereto.

The polyclonal antibody may be produced by a method well known in the art, which includes injecting the protein antigen into an animal and collecting blood from the animal to obtain a serum containing the antibody. Such polyclonal antibodies may be prepared from any animal species host such as goat, rabbit, sheep, monkey, horse, pig, cow, dog, etc., but it is not limited thereto.

Further, the antibody of the present invention may include a special antibody such as a chimeric antibody, a humanized antibody, or a human antibody.

The "peptide" has an advantage of high binding strength to a target material, and involves no occurrence of denaturation even during heat/chemical treatment. Further, because of a small molecular size of the peptide, it can be bonded to other proteins and used as a fusion protein. Specifically, it may be used as a diagnostic kit and drug delivery material because it can be used by binding it to a polymer protein chain.

The "aptamer" refers to a kind of polynucleotide consisting of a special type of single-stranded nucleic acid (DNA, RNA or modified nucleic acid) that has a stable tertiary structure and is bound to a target molecule with high affinity and specificity. As described above, the aptamer may be specifically bound to an antigenic substance in the same way as the antibody, but has higher stability than the protein with a simple structure. Further, this is composed of a polynucleotide that is easy to synthesize, thereby being usable as an alternative to an antibody.

The anticancer agent is the same as described above.

The present invention provides a kit for diagnosing resistance to DNA replication inhibitory anticancer agents, which includes the above-described composition.

The kit may include not only a material specifically bound to the tristetraprolin gene or a protein thereof, but also one or more other constitutional compositions, solutions or devices suitable for an assay method to measure an expression level of tristetraprolin gene or a protein thereof used in the kit.

When the kit is a kit for measuring the expression level of tristetraprolin gene or a protein thereof, it may be a kit including essential elements necessary for executing RT-PCR. In addition to each primer pair specific for mRNA of a marker gene, the RT-PCR kit may include a test tube or other suitable container, reaction buffer, deoxyribonucleotides (dNTPs), enzymes such as Taq-polymerase and reverse transcriptase, DNase, RNase inhibitors, DEPC-water (dEPC water), sterile water and the like. Further, a pair of primers specific to a gene used as a quantitative control may be included.

The kit may include: a nucleotide sequence of a gene encoding tristetraprolin; a sequence complementary to the above nucleotide sequence; and a substrate, a suitable buffer solution, a secondary antibody labeled with a chromogenic enzyme or a fluorescent substance and a chromogenic substrate in order to implement immunological detection of a material specifically bound to a fragment of the nucleotide or a protein encoded by the nucleotide sequence. As the substrate, a nitrocellulose membrane, a 96-well plate synthesized from a polyvinyl resin, a 96-well plate synthesized from a polystyrene resin, and a glass slide glass, etc. may be used, while the chromogenic enzyme used herein may include, for example, peroxidase, alkaline phosphatase, etc. Further, as the fluorescent substance, FITC, RITC, etc. may be used, while the chromogenic substrate used herein may include, for example, 2,2'-azino-bis(3-ethylbenzothiazoline-6-sulfonic acid) (ABTS) or o-phenylenediamine (OPD), tetramethyl benzidine (TMB) and the like.

The kit may be a microarray for diagnosing anticancer agent resistance, which is able to measure the expression level of tristetraprolin gene. The microarray may be easily prepared by those skilled in the art according to a method known in the art using the above index factor.

Further, the kit of the present invention may include an antibody specifically bound to a marker component, a secondary antibody conjugate to which a label developing color by a reaction with a substrate is conjugated, a chromogenic substrate solution to react with the label, a washing solution, an enzyme reaction stopping solution, and the like, and may be manufactured as a plurality of separate packaging or compartments in which the reagent components to be used are contained, but it may not be limited thereto.

The kit of the present invention may include an agent capable of measuring the expression level of tristetraprolin gene or a protein thereof in a patient sample, as well as one or more types of compositions, solutions or devices suitable for analysis of the expression level. For example, the kit may include a substrate, an appropriate buffer solution, a secondary antibody labeled with a detection label, a chromogenic substrate, etc., in order to implement immunological detection of the antibody, but it may not be limited thereto.

As a specific example, the kit may be a kit including essential elements necessary for performing ELISA in order to implement various ELISA methods such as an ELISA kit and a sandwich ELISA. These ELISA kits may include antibodies specific for the above proteins. The antibody is an antibody with high specificity and affinity for tristetraprolin while having little cross-reactivity with other proteins, and may be a monoclonal antibody, a polyclonal antibody or a recombinant antibody.

The ELISA kit may also include an antibody specific to a control protein. Each of other ELISA kits may include a reagent capable of detecting bound antibodies, for example, a labeled secondary antibody, chromophores, an enzyme and other substances capable of binding to their substrates or antibodies, etc., but it may not be limited thereto.

Alternatively, the above kit may be a kit for implementing Western blot, immunoprecipitation assay, complement fixation assay, flow cytometry, or protein chip, etc., and may further include additional configurations suitable for the above assay methods. Through these analysis methods, anticancer agent resistance can be diagnosed by comparing amounts of antigen-antibody complex formation.

The present invention may provide an information providing method for diagnosing resistance to DNA replication inhibitory anticancer agents, which includes measuring an expression level of tristetraprolin gene or a protein thereof in a sample isolated from a diagnostic subject.

The diagnostic subject may be a patient who is currently being treated with the DNA replication inhibitory anticancer agent, a patient who has been treated with the DNA replication inhibitory anticancer agent, and other patients who want to receive information for diagnosing resistance to the DNA replication inhibitory anticancer agent, etc. Preferably, the subject may be a patient diagnosed with colorectal cancer or lung cancer.

The cancer may be a solid cancer, preferably selected from the group consisting of lung cancer, ovarian cancer, colorectal cancer, colon cancer, pancreatic cancer, liver cancer, cervical cancer, kidney cancer, gastric cancer, prostate cancer, breast cancer, brain tumor, uterine cancer and bladder cancer, and more preferably selected from the group consisting of colorectal cancer and lung cancer.

The sample is isolated from the diagnostic subject, and examples thereof may include tissue, cells, blood, serum, plasma, saliva, or urine, but it is not limited thereto.

The composition of the present invention is a material for predicting whether the anticancer agent administration can consistently implement the same anticancer effects in a patient group treated with the DNA replication inhibitory anticancer agent, and may be used to predict the reactivity to an anticancer agent by treating the sample isolated from the diagnostic subject with the composition and then measuring an expression level of tristetraprolin gene or a protein thereof in the sample.

With regard to the method for the present invention, if the measured expression level is higher than that of a control, it can be determined that the diagnostic subject has higher resistance to the DNA replication inhibitory anticancer agent than the control. For example, if the expression level of tristetraprolin gene or a protein thereof in a sample isolated from a specific patient in the patient group who receive administration of the DNA replication inhibitory anticancer agent is higher than that of other patients, it may be determined that the patient is more resistant to the anticancer agent than other patients.

The above measurement may be performed by treating the sample with a substance for detecting tristetraprolin gene or a protein thereof.

The substance for detecting tristetraprolin gene or a protein thereof may be within the range exemplified above.

The diagnostic subject and anticancer agent are the same as described above.

As the method for measuring the expression level of tristetraprolin gene or a protein thereof, a method for measuring a concentration of mRNA, which is a transcription material of the gene encoding tristetraprolin, or a concentration of the tristetraprolin protein in the sample may be selected, but it is not limited thereto. Therefore, any method commonly used in the technical field of the present invention may be selected and used.

The method for measuring the concentration of mRNA in the sample may include, for example, reverse transcriptase polymerase chain reaction (RT-PCR), competitive reverse transcriptase polymerase chain reaction (Competitive RT-PCR), real-time reverse transcriptase polymerase chain reaction (Real-time RT-PCR), RNase protection assay (RPA), Northern blotting and DNA chip, but it is not limited thereto.

As the method for measuring the concentration of the protein in the sample, an amount of the protein may be determined using an antibody specifically bound to the protein. Analysis methods for this purpose may include, for example, immunoblot test, sandwich assay, enzyme linked immunosorbent assay (ELISA), radioimmunoassay (RIA), radial immunodiffusion, Ouchterlony immunediffusion method, rocket immunoelectrophoresis, tissue immunohistochemistry, immunoprecipitation assay, complement fixation assay, fluorescence-activated cell sorting (FACS), Western blotting, flow cytometry, enzyme substrate coloring, antigen-antibody aggregation, protein chip, etc., and preferably enzyme linked immunosorbent assay (ELISA) is used, but it is not limited thereto.

Hereinafter, the following examples will be given to describe the present invention in detail.

Example 1. Confirmation of Deterioration in Phosphorylation Performance of CHK1 in Response to Genotoxic Stress by Tristetraprolin (TTP) Knockdown The two DNA damage response kinases ATR and ATM play key roles in the protection of genomic integrity from genotoxic stress by sensing a single-strand break and DSB (Double strand break), respectively. To identify the functions of TTP in the DNA damage response, we first analyzed the phosphorylation levels of CHK1 (p-CHK1) and CHK2 (p-CHK2) as readouts of ATR and ATM activity, respectively.

After depletion of TTP using siRNA consisting by SEQ ID NO: 1 or SEQ ID NO: 2, we observed significant downregulation of p-CHK1 but not of p-CHK2 upon UV irradiation, which typically triggered activation of both ATR and ATM pathways as seen in the upregulation of both p-CHK1 and p-CHK2 at 2 hours after treatment (FIG. 1A). These results suggest that TTP may be involved in the ATR-CHK1 pathway.

Figure 1C:
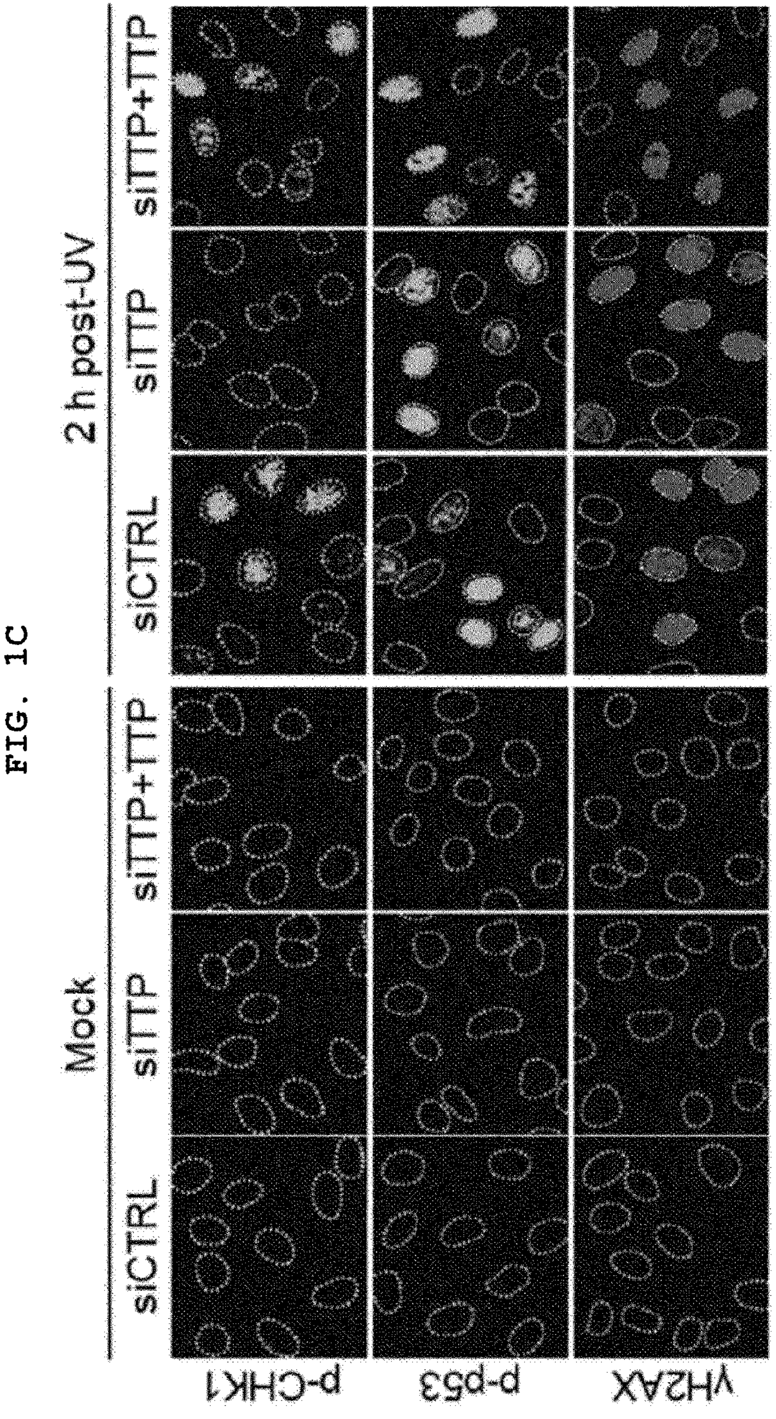
Figure 1D:
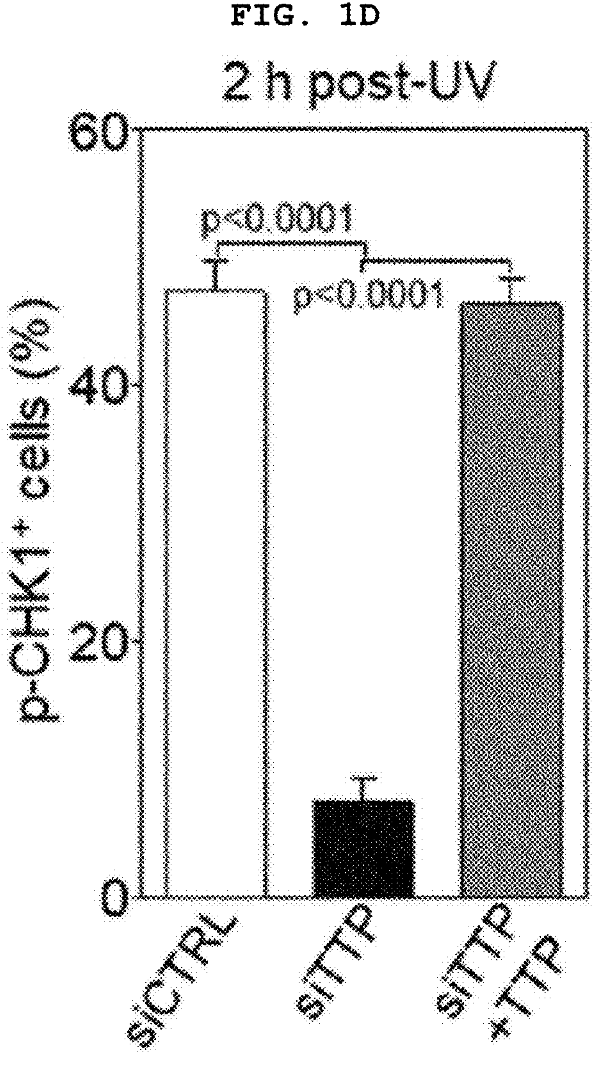
Figure 1E:
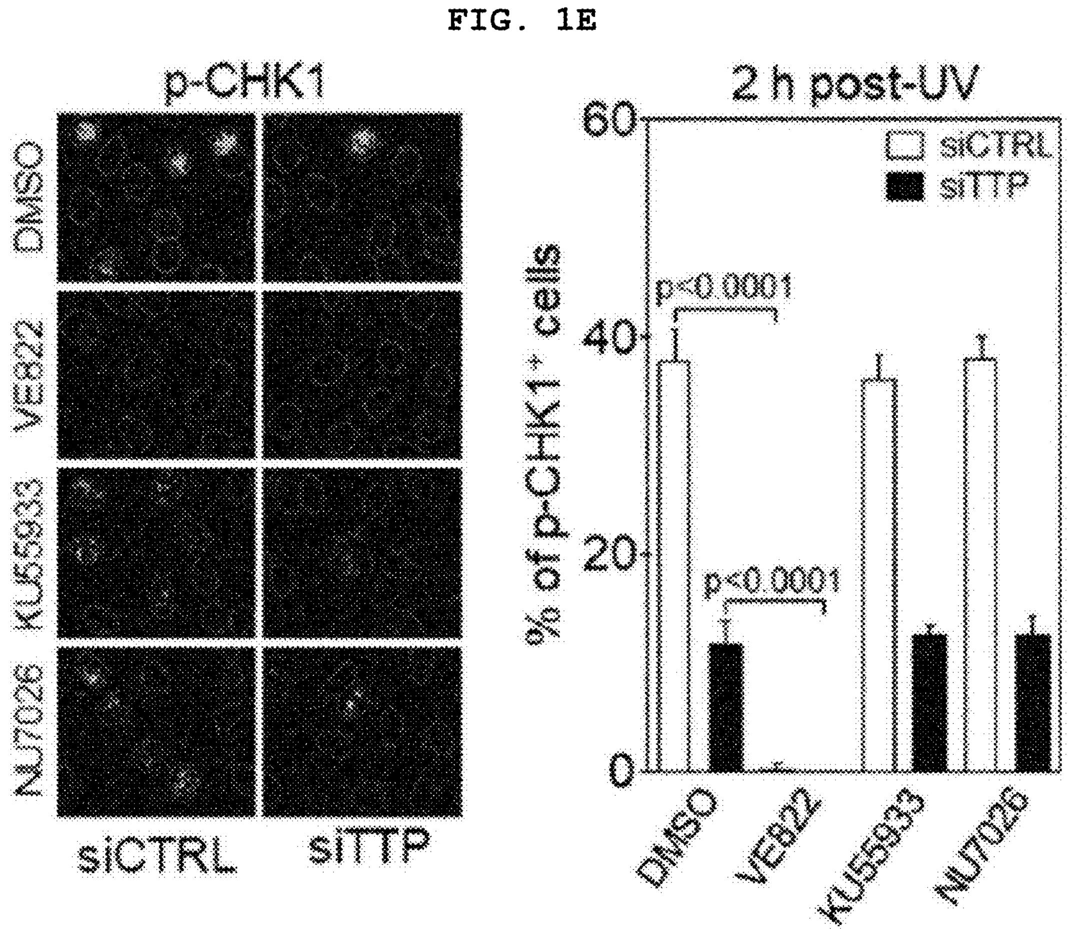

We also analyzed major ATR substrates other than CHK1, including p-p53 and γH2AX, but the changes from these substrates were marginal (FIG. 1A). Importantly, ectopic expression of siRNA-resistant TTP in TTP-deficient cells fully restored the p-CHK1 level in response to UV as compared to the control cells (FIG. 1B). In line with the immunoblot data, an immunocytochemistry analysis also confirmed that TTP is required selectively for CHK1 phosphorylation upon UV irradiation (FIGS. 1C and 1D), whereas no significant phosphorylation of ATR substrates was observed in the absence of exogenous DNA damage in TTP-deficient cells (FIG. 1C). Moreover, only in the presence of the ATR inhibitor (VE-822), but not ATM (KU55933) or DNA-PK inhibitor (NU7026), the residual p-CHK1 signal was vanished in TTP-deficient cells (FIG. 1E), supporting that TTP regulates the ATR-CHK1-dependent DNA damage response.

Figure 1F:
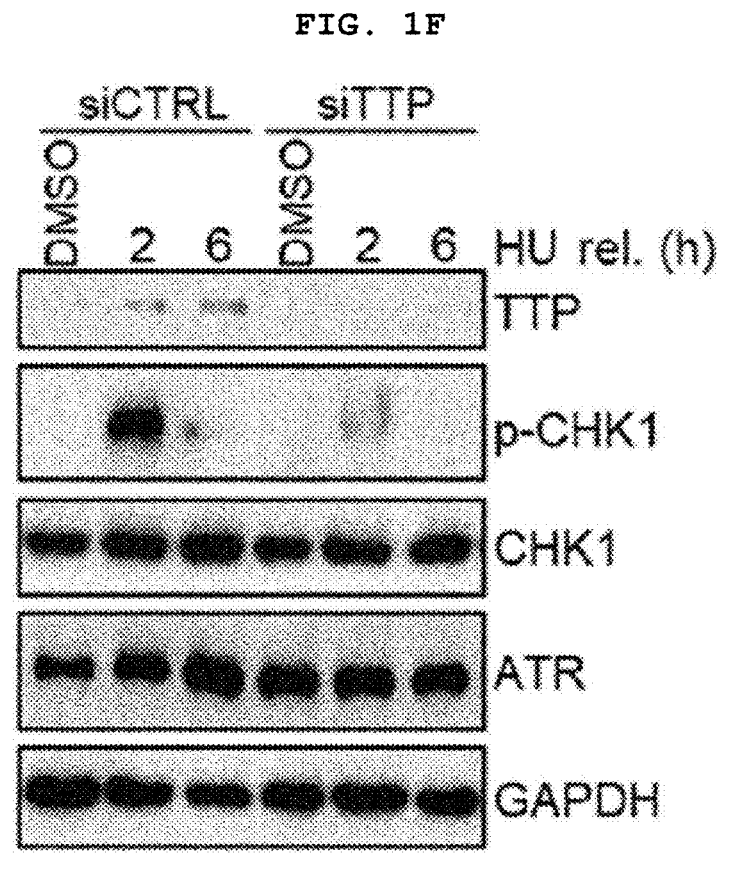

Then, we treated cells with HU, another CHK1 phosphorylation-triggering agent which depletes the deoxynucleoside triphosphate pool, thus inducing the RSR (Replication Stress Response). At 2 h after HU treatment, the control cells showed a robust p-CHK1 formation, but the TTP-deficient cells exhibited compromised p-CHK1 formation without altering total CHK1 or ATR protein levels (FIG. 1F).

Example 2. Identification of the Role of TTP in Replication Stress Response (RSR)

(1) ATR-CHK1 pathway accounts for the central replication stress responses and once activated it helps the cell to survive and faithfully complete DNA replication under stress. Having shown that TTP is found to be implicated in the ATR-CHK1 activation, as in Example 1 above, we decided to examine the effect of TTP on the replication fork stability using DNA fiber analysis, the clearest read-out of replication stress which relies on the incorporation of nucleotide analogues. The replicating DNA was labeled with IdU for 20 min and then either exposed to 20 J/$m^2$ UV or mock-treated and labeled concomitantly with CldU for 40 min.

Figure 2A:
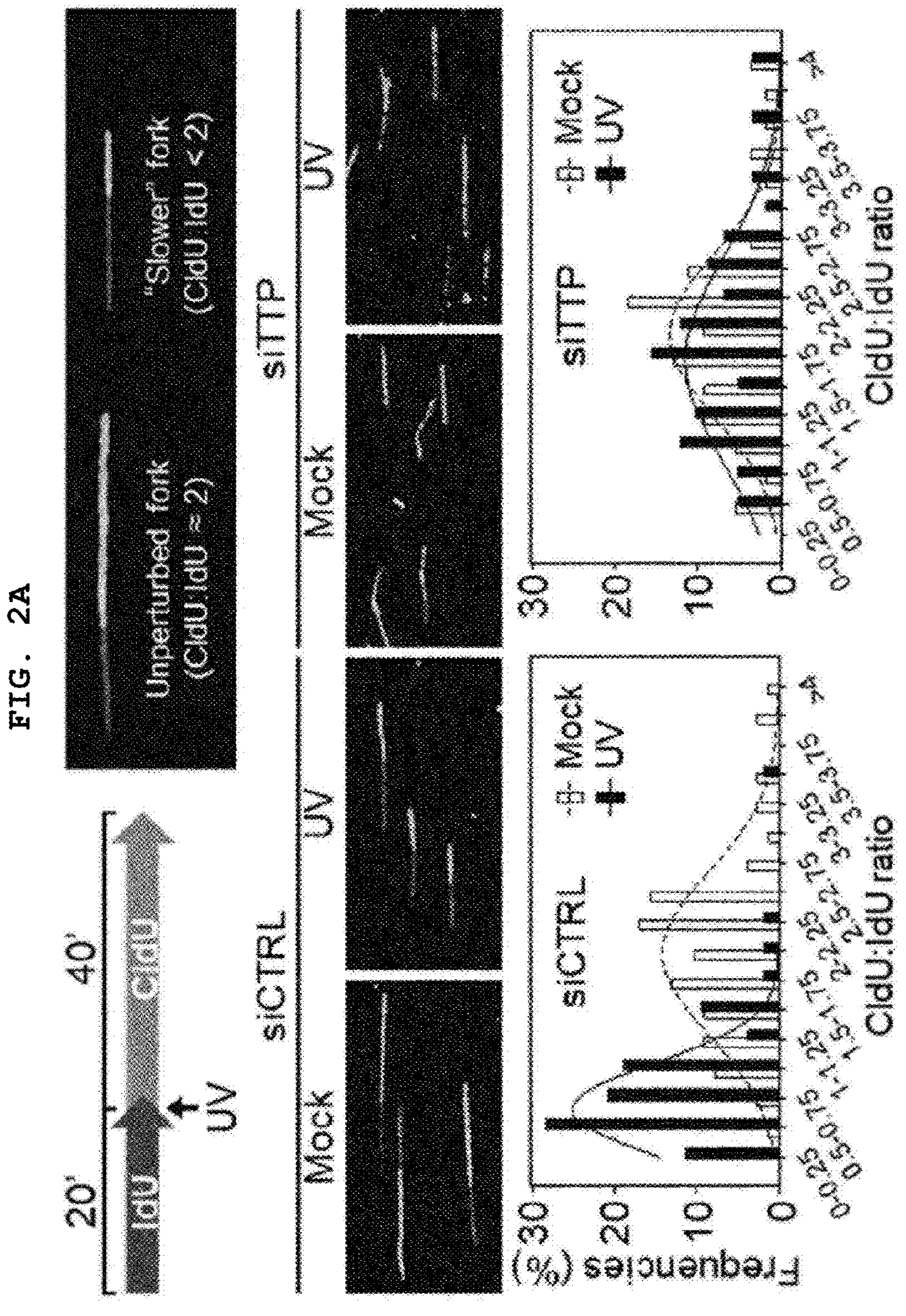
FIGS. 2A to 2D correspond to Example 2.

There was no overt difference in the mean CldU:IdU ratio of the mock treated cells both from control—(1.92, Group introduced with siRNA consisting of SEQ ID NO:3) and TTP-deficient (1.94) cells showing almost twice longer CldU-labeled fibers than those labeled with IdU (FIG. 2A). UV irradiation can stimulate the ATR mediated intra S checkpoint to slow down the elongation of DNA synthesis until the damages are resolved. As expected, UV treatment resulted in the dramatic reduction in the mean CldU:IdU ratio in control cells that is close to 0.75, however, TTP-depleted cells exhibited almost no reduction in the ratio (1.81) that is comparable to the mock-treated CldU:IdU ratio (FIG. 2A). These results indicate that TTP is required for the ATR-CHK1 function in slowing down the fork speed in response to replication stress.

(2) ATR-CHK1 pathway is also implicated for the restart of stalled replication forks after the damage is tolerated or removed by repair systems. To test whether TTP participates in fork restart, we treated cells with 4 mM HU for 2 h between IdU- and CldU-labeling procedures. To quantify fork restart rates, the number of stalled forks (IdU-only fibers) on the intact single-strand DNA (blue) was normalized to the total number of replication forks.

Figure 2B:
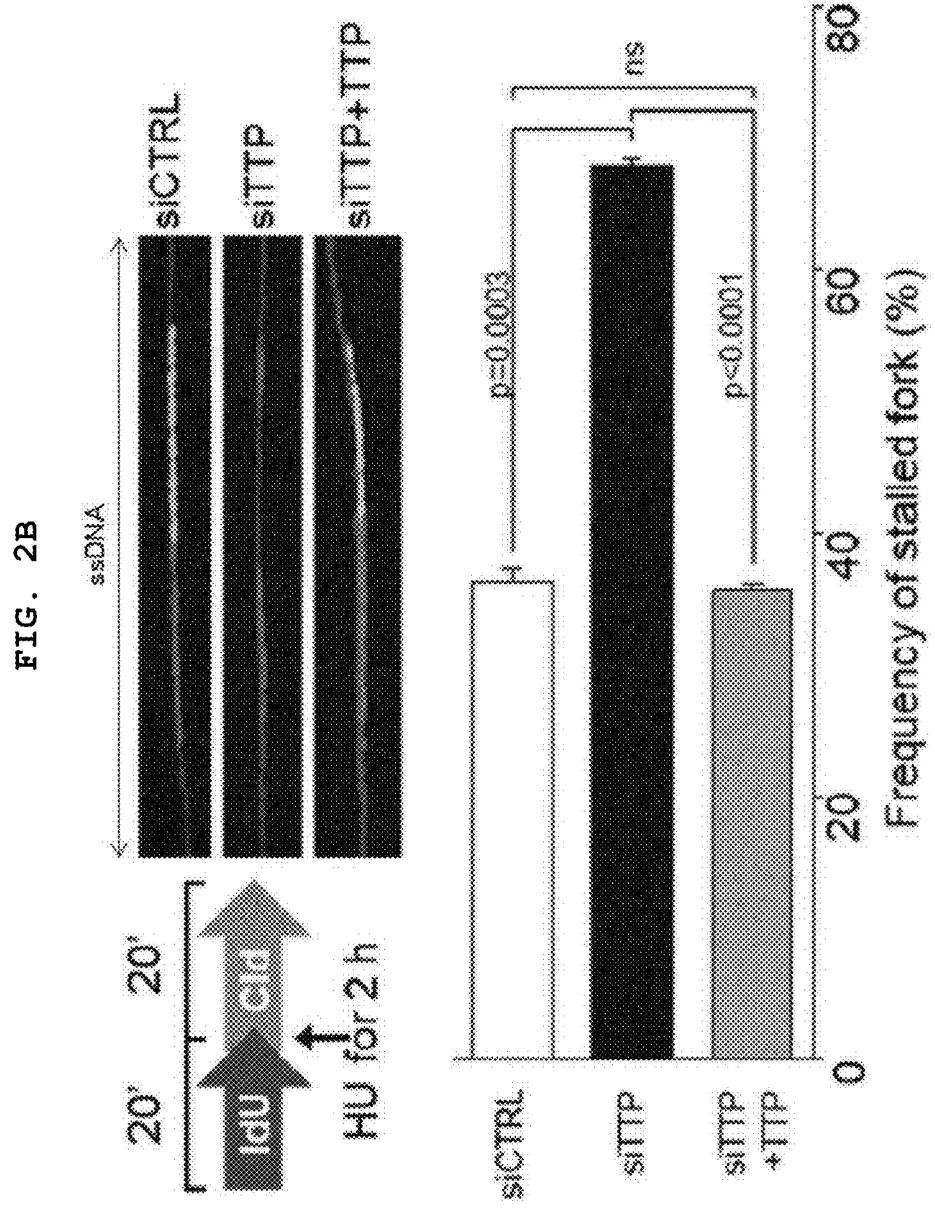
Figure 2C:
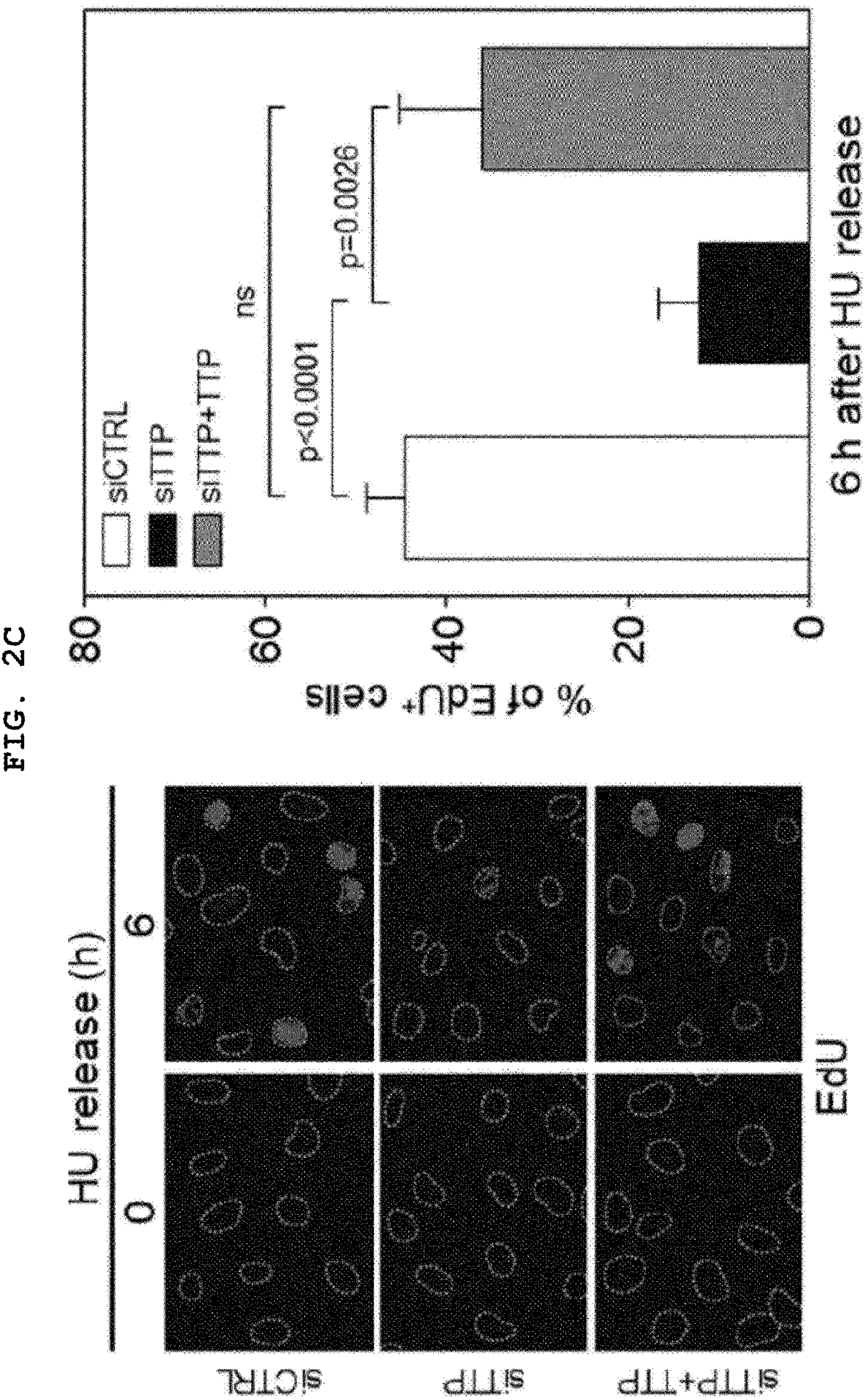

The results revealed that TTP-deficient cells yielded approximately twofold more stalled forks than control cells did, and re-expression of siRNA-resistant TTP offset this defect (FIG. 2B). The failure of the restart of a stalled fork possibly impedes S phase progression. Indeed, an EdU incorporation assay aimed at assessing the number of cells with resumed DNA synthesis revealed an overt difference between the control and TTP knockdown cells with approximately 50% and 10% of EdU-positive cells, respectively (FIG. 2C).

(3) We next examined the involvement of TTP in stalled fork protection. Replicating DNA was sequentially labeled with IdU and CldU for 20 min each, followed by HU treatment for 6 h to stall replication forks. We then analyzed the relative shortening of CldU fiber as indicative of fork degradation.

Figure 2D:
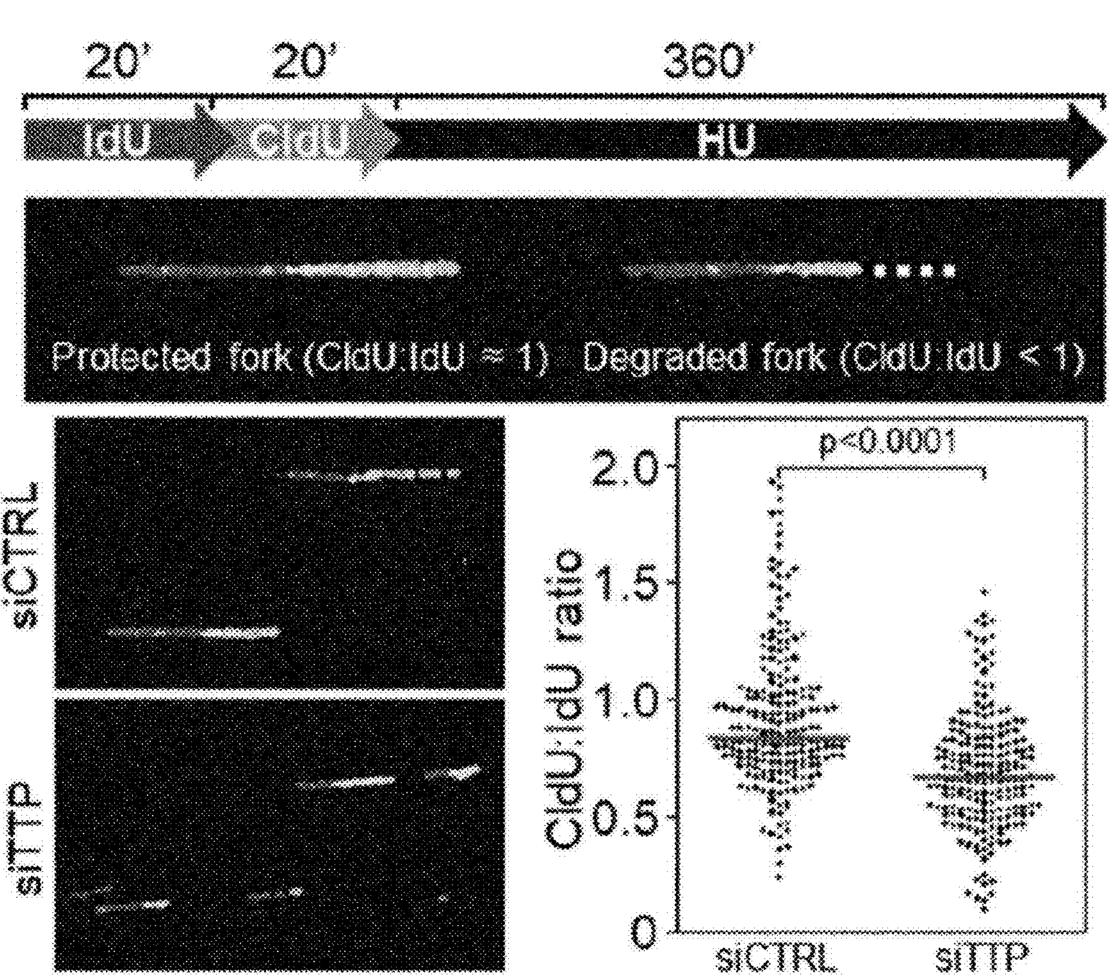

As presented in FIG. 2D, the replication forks in control cells were well protected as shown in the median CldU:IdU ratio close to 1.0 (0.8) whereas TTP-deficient cells featured a significant decrease of the ratio (0.67). These results indicate that TTP is required for the stability and restart of stalled forks during the RSR.

Example 3. Confirmation of the Role of TTP on the Stabilization of Claspin mRNA (1) The combined data from our current results implicating TTP as a potential mediator for ATR-CHK1 pathway and previous studies demonstrating Claspin as the key mediator of ATR-dependent CHK1 phosphorylation under replication stress led us to speculate the possibility that TTP may regulate ATR-CHK1 activity via posttranscriptional control of Claspin mRNA.

Figure 3A:
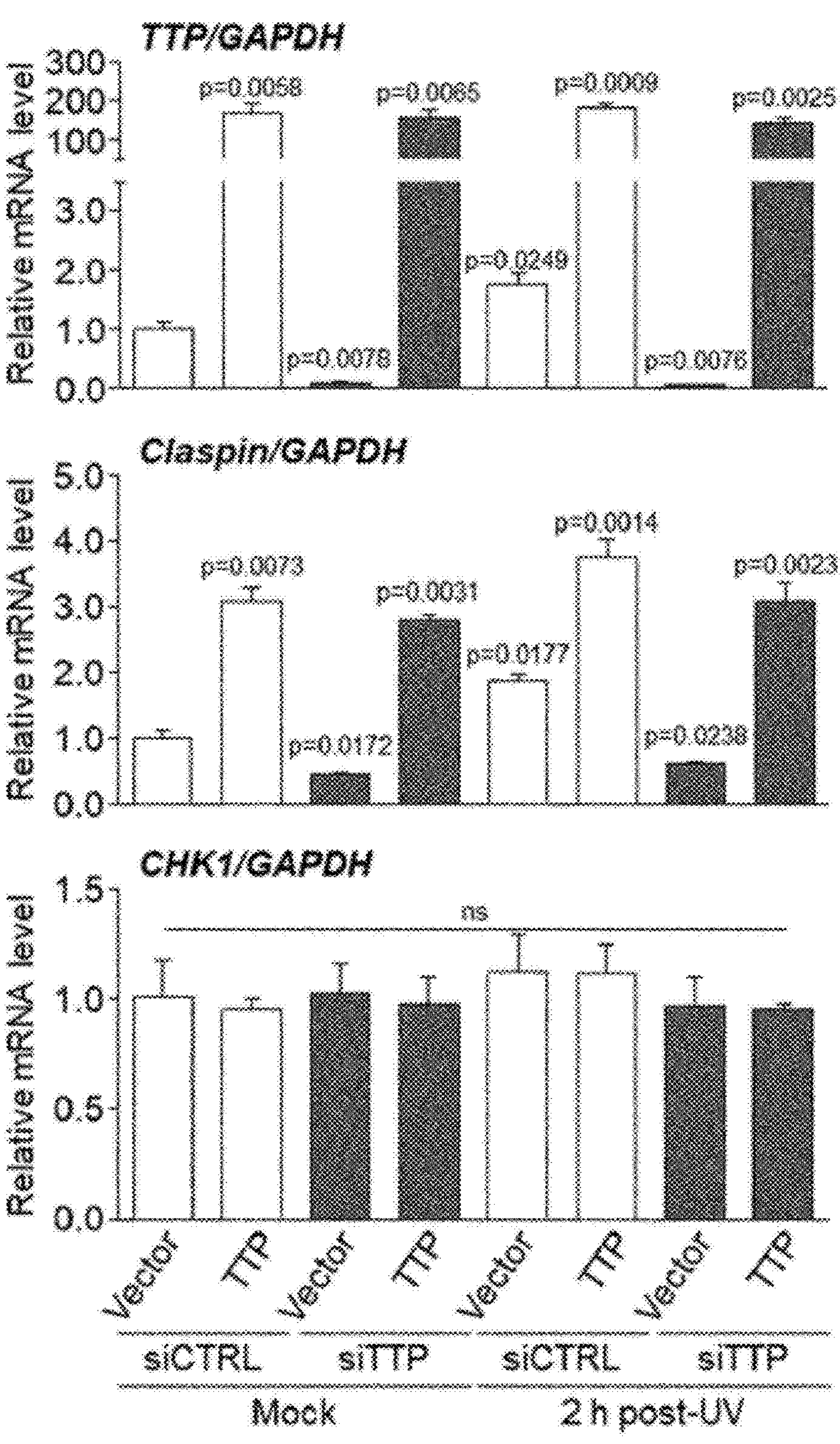
FIGS. 3A to 3E correspond to Example 3.

To test this idea, we employed a quantitative real-time PCR to monitor the amounts of Claspin mRNA in the absence of exogenous DNA damage (mock) and at 2 h after UV exposure when CHK1 phosphorylation peaked (FIGS. 1A to 1F). The primer sets of SEQ ID NOs: 6 and 7 were used for amplification of Claspin mRNA. Both from with and without DNA damage, a slight decrease in the total amount of Claspin mRNA was apparent in TTP-deficient cells, and this amount was almost fully recovered by re-expression of TTP (FIG. 3A). It was noteworthy that the dynamic alteration of the Claspin mRNA amount was highly correlated with the cellular concentration of TTP mRNA (FIG. 3A).

Figure 3B:
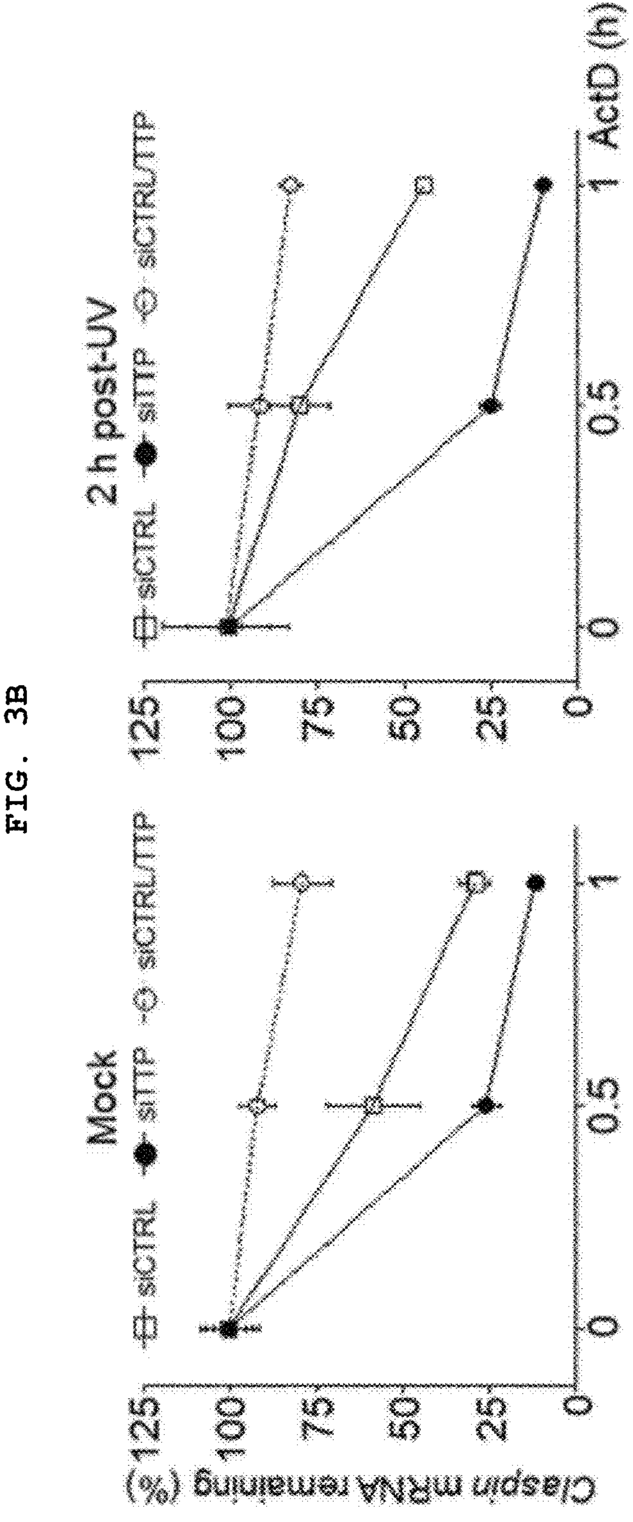

(2) The half-life of Claspin mRNA in unperturbed cells was moderately decreased upon TTP depletion, however, that was dramatically increased by overexpression of the siRNA (siRNA consisting by SEQ ID NO: 1 or SEQ ID NO: 2)-resistant TTP in TTP-deficient cells (FIG. 3B). TTP-dependent regulation of Claspin mRNA stability was also observed in the presence of UV damage, supporting that TTP is required for Claspin mRNA stabilization.

Figure 7:
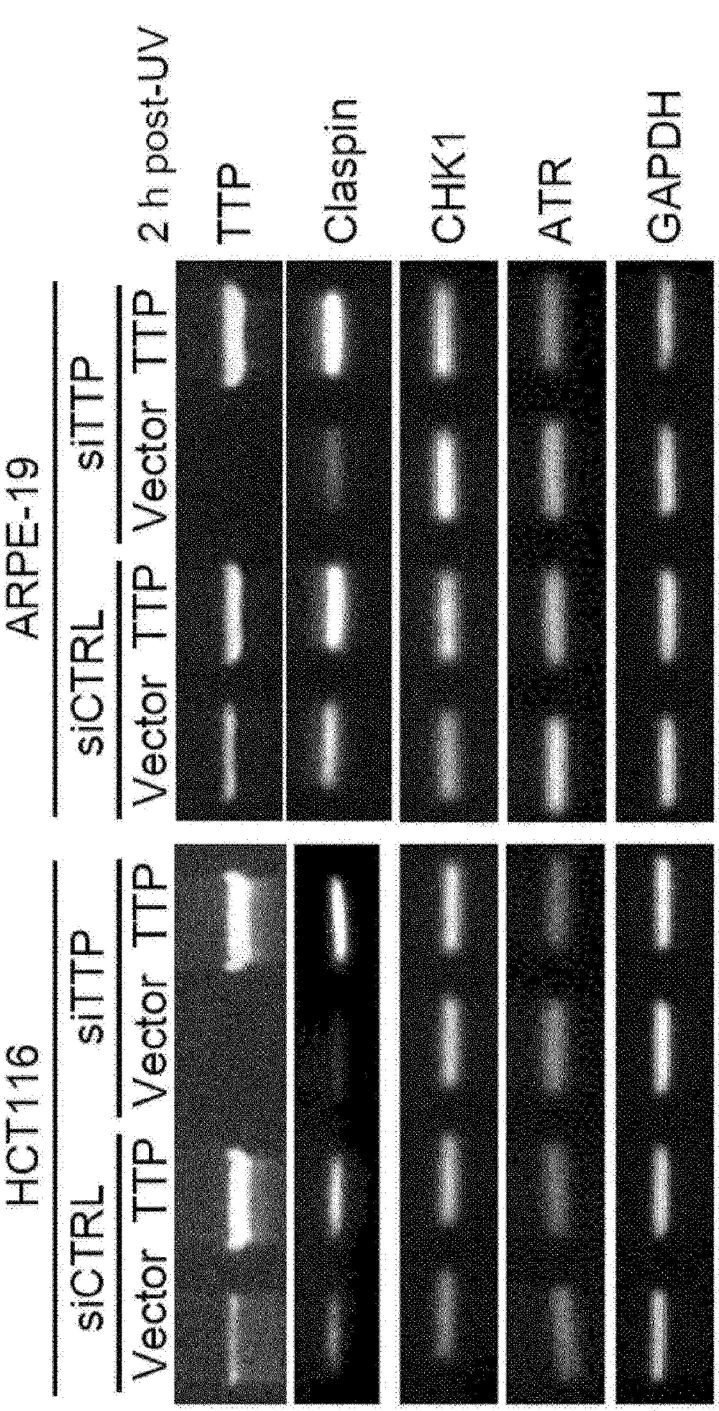
FIG. 7 shows the result of the RT-PCR of the mRNA levels of the indicated genes of HCT116 (human colorectal carcinoma) or ARPE-19 cells (the normal epithelial cells) co-transfected with either siCTRL or siTTP and either the control vector(empty vector) or vector expressing siRNA-resistant TTP.

We also investigated the TTP effect on the regulation of Claspin mRNA stability in response to genotoxic stress with two different human cell lines HCT116 (colon cancer) and ARPE-19 (normal epithelial) cells (FIG. 7) and uncovered that TTP-mediated regulation of Claspin mRNA stability is operating in these cells too, which implicates that these phenotypes are not cell line dependent.

Figure 8:
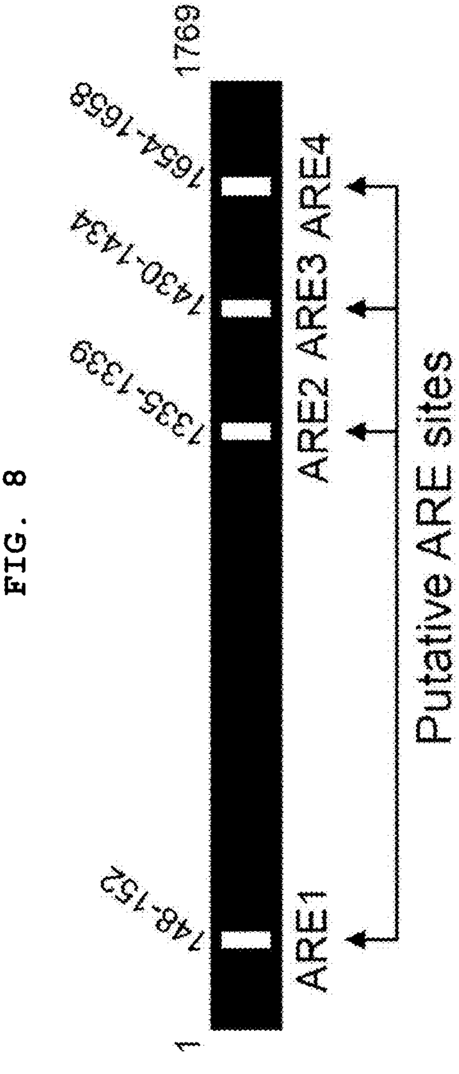
FIG. 8 shows the locations of putative AREs in the Claspin mRNA.

(3) Claspin mRNA contains four conserved AREs in the 3'UTR for putative TTP binding (FIG. 8). To investigate whether TTP can directly bind to the 3'UTR of Claspin mRNA, TTP-bound RNAs were subjected to immunoprecipitation with an anti-TTP antibody, and the four different AREs were amplified by reverse-transcription PCR. GAPDH mRNA was used as a negative control and was amplified by PCR with a primer set of SEQ ID NOs: 10 and 11.

In the reverse transcription PCR, ARE1 was amplified using a primer set of SEQ ID NOs: 12 and 13, ARE2 was amplified using a primer set of SEQ ID NOs: 14 and 15, ARE3 was amplified using a primer set of SEQ ID NOs: 16 and 17, and ARE4 was amplified using a primer set of SEQ ID NOs: 18 and 19, respectively.

Figure 3C:
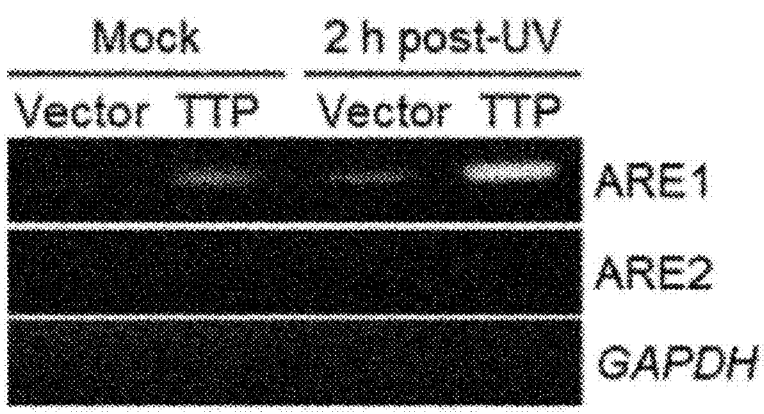

Among the four AREs, only ARE1, which is located most closely to the stop codon of Claspin mRNA, was amplified successfully (FIG. 3C). To determine whether stabilization of Claspin mRNA indeed depends on the direct binding of TTP to Claspin ARE1, TTP-deficient and TTP-overexpressing cells were transfected with a luciferase reporter gene containing either wild-type ($ARE1^{WT}$) or mutated Claspin ARE1 ($ARE1^{Mut}$)

Figure 3D:
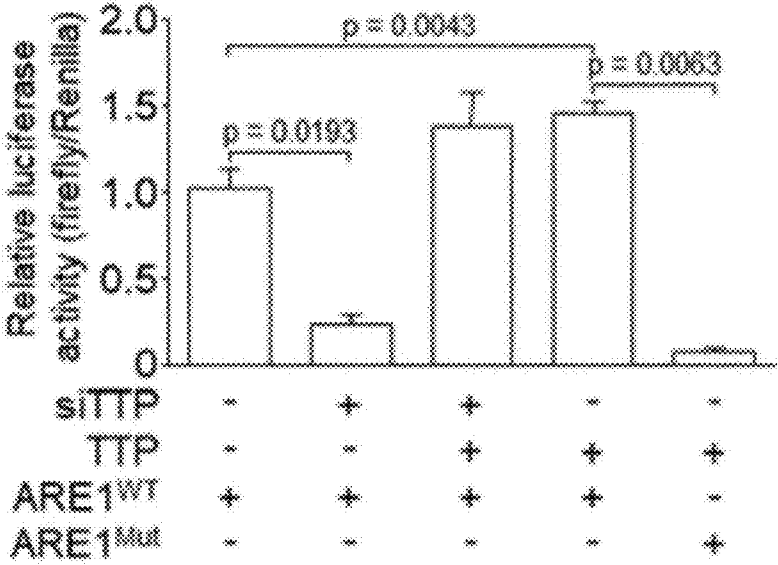

In cells expressing the luciferase mRNA with Claspin $ARE1^{WT}$, the luciferase activity diminished approximately five-fold after TTP depletion (FIG. 3D). TTP overexpression either in control or TTP knockdown cells significantly increased the luciferase signals (FIG. 3D). By contrast, TTP overexpression in $ARE1^{Mut}$cells failed to induce luciferase activity (FIG. 3D).

Figure 3E:
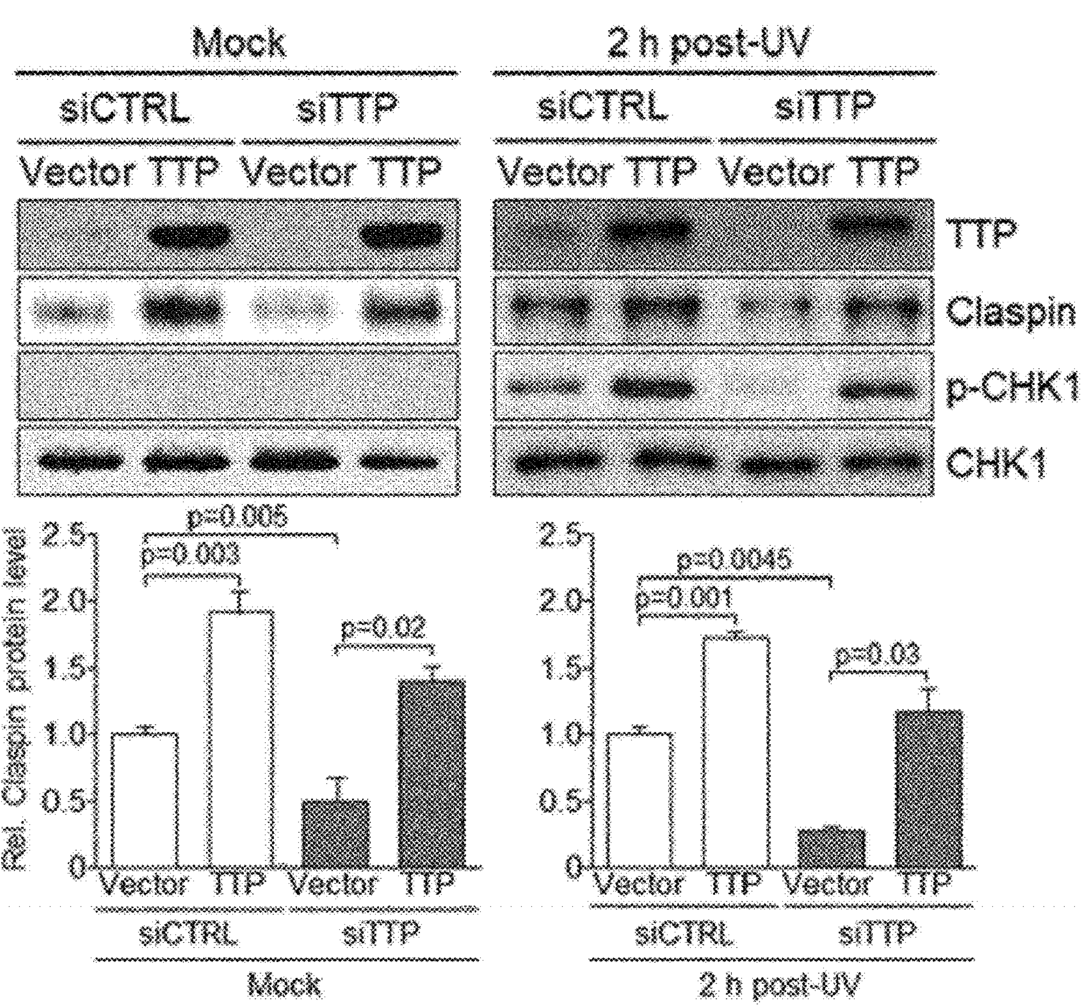

These data suggest that TTP promotes Claspin mRNA expression through direct binding to ARE1 in the 3'UTR. In addition, we observed that the protein level of Claspin was tightly controlled by the cellular concentration of TTP both in the presence and absence of genotoxic stress (FIG. 3E). Taken together, these results suggest that TTP maintains Claspin mRNA levels via stabilization of its 3'UTR.

Figure 4A:
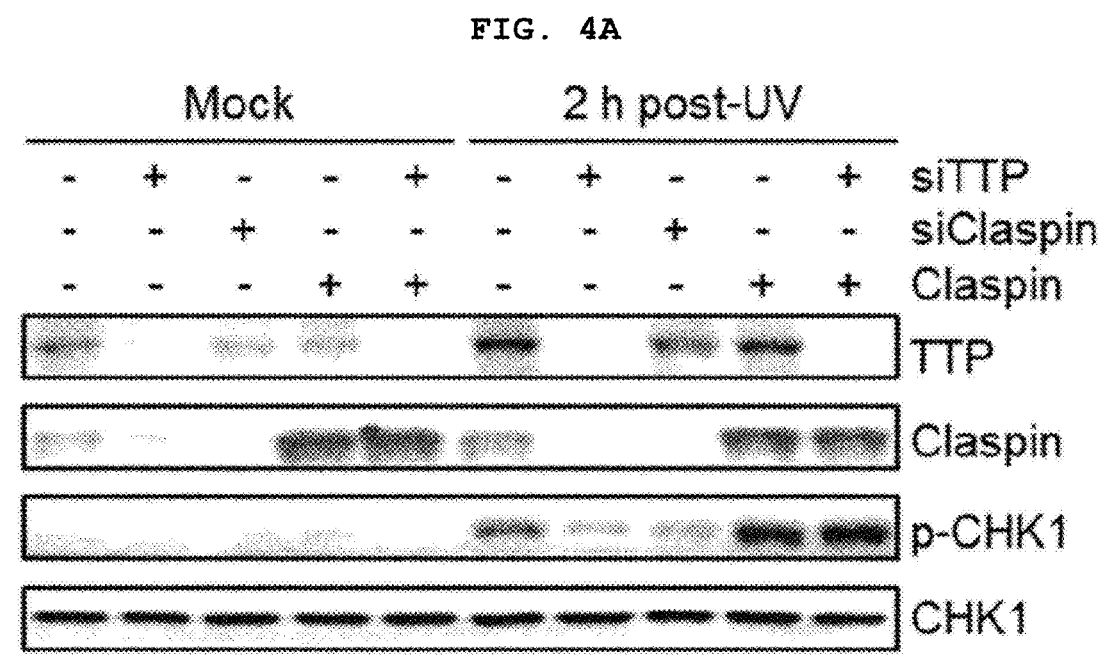
Figure 4B:
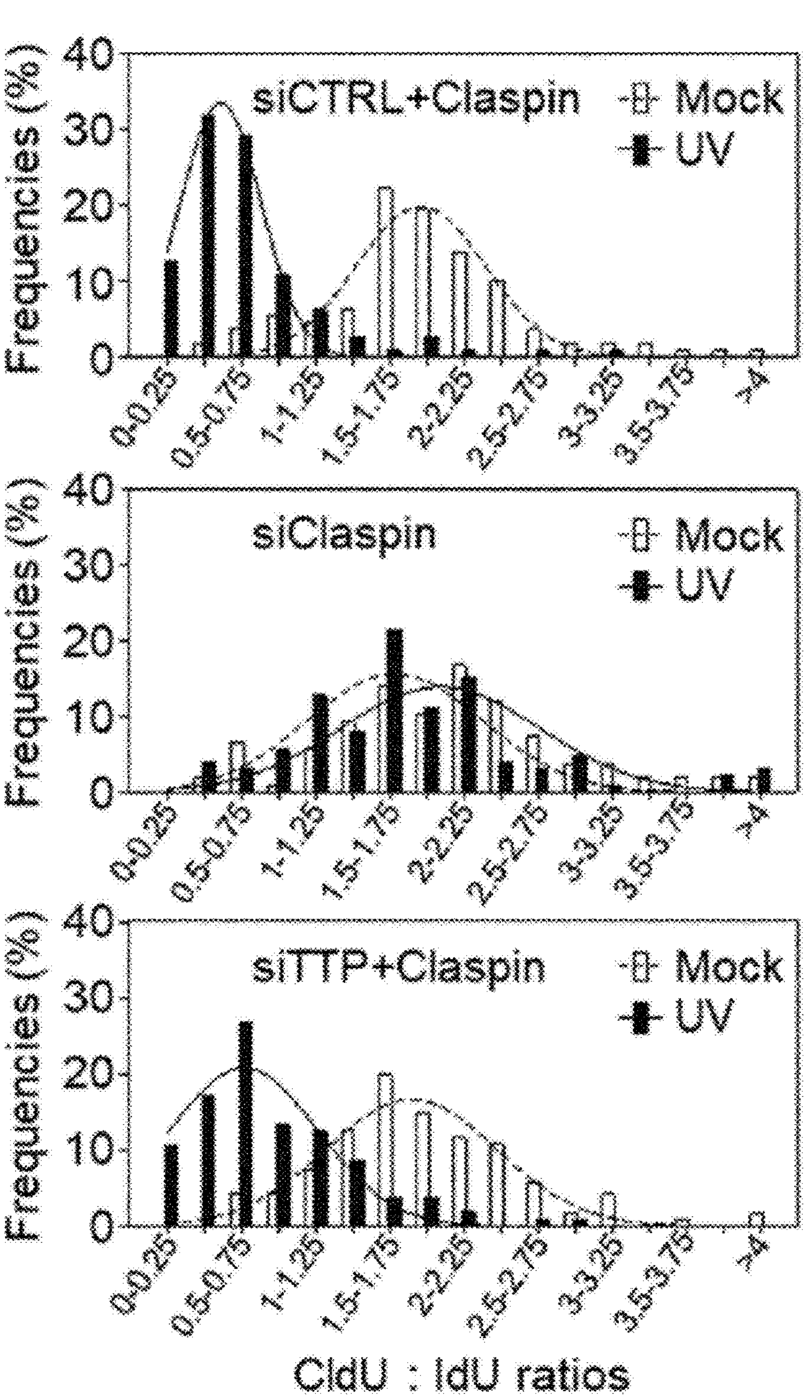
Figure 4C:
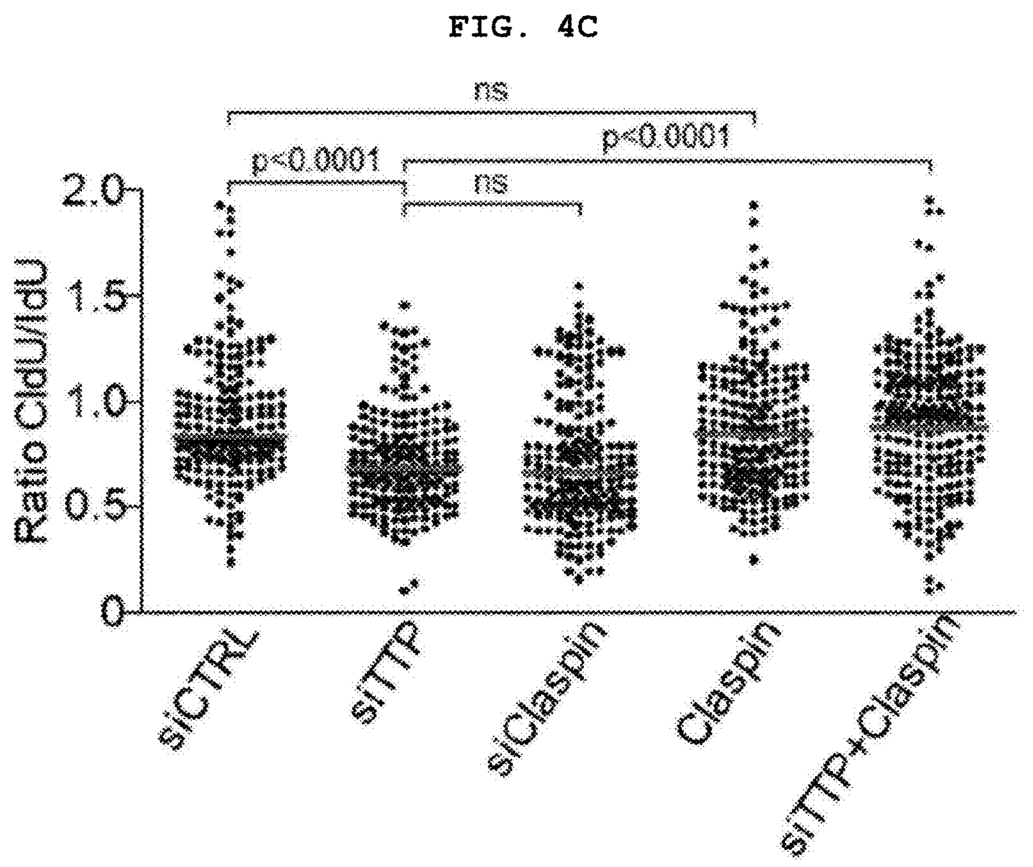

(4) Next, in order to confirm whether TTP regulation of the RSR is indeed mediated by Claspin, we decided to investigate the effect of Claspin overexpression in the CHK1 phosphorylation, replication fork slowing and protection in Claspin-deficient cells. The reduced CHK1 phosphorylation upon TTP depletion was fully restored by Claspin overexpression (FIG. 4A). Claspin-deficient cells were made by introducing siClaspin (SEQ ID NO: 20) into cells, and then introduced into a vector expressing siRNA-resistant Claspin to overexpress Claspin. Besides, the impaired fork slowing and fork protection in TTP- or Claspin-deficient cells upon DNA damage was also successfully recovered by Claspin overexpression (FIGS. 4B and 4C).

Figure 5A:
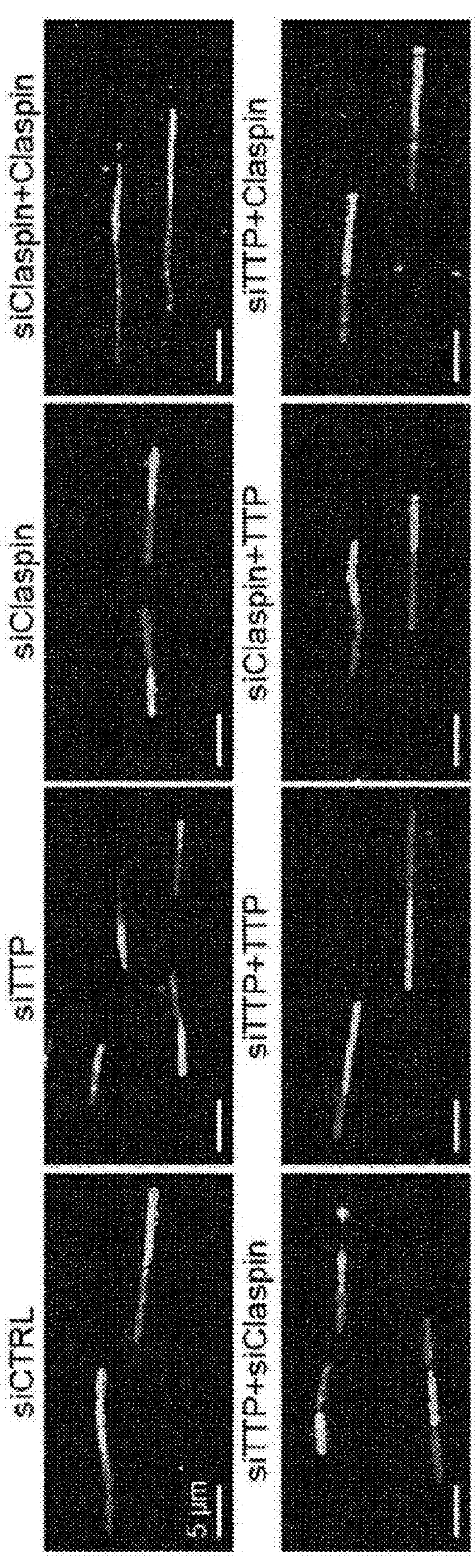
FIGS. 5A and 5B correspond to Example 4. A549 (human lung carcinoma) cells transfected with the indicated siRNAs were cotransfected with the empty vector or vector expressing siRNA-resistant TTP. The transfected cells were sequentially pulse-labeled with IdU and CldU, each for 20 min.
Figure 9:
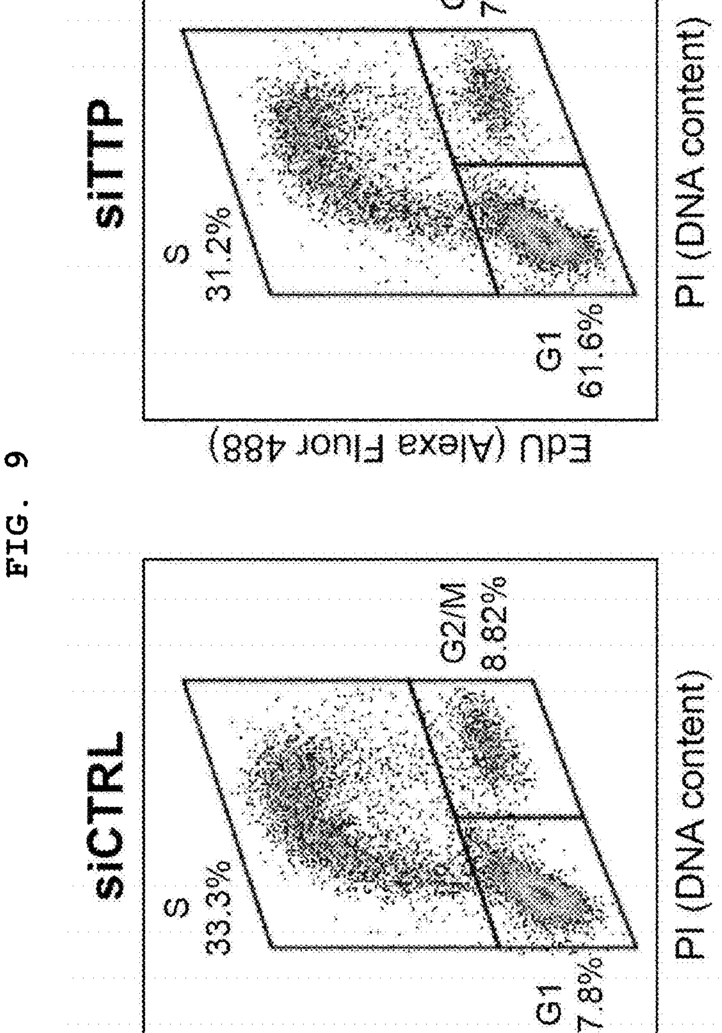
FIG. 9 shows the representative cell cycle profiles of siCTRL- or siTTP-transfected A549 (human lung carcinoma) cells. Either siCTRL- or siTTP-transfected cells were labeled with EdU for 2 h and harvested. The cells were stained with Alexa 488 azide to detect EdU incorporation and with propidium iodide (PI) to detect DNA. Representative graph shows EdU incorporation on the y-axis and total DNA on the x-axis.

Example 4. Identification of the Role of TTP in Prolongation of the Replication Bifurcation in Inactive Cells As shown in FIG. 9, similarly to the cell cycle profiles from Claspin knockdown cells, we observed TTP knockdown itself in unperturbed cells did not significantly disturb cell cycle progression either. However, Claspin is required for stable elongation of the replication fork in vertebrate cells during the normal S phase. We found that TTP regulates Claspin expression after DNA damage as well as in unperturbed condition (FIG. 9), and this finding raised the possibility that TTP-mediated Claspin regulation is also involved in replication fork progression in unperturbed cells. To test this hypothesis, we analyzed replication fork velocity in TTP- and/or Claspin-depleted cells with DNA fiber analysis (FIG. 5A).

Figure 5B:
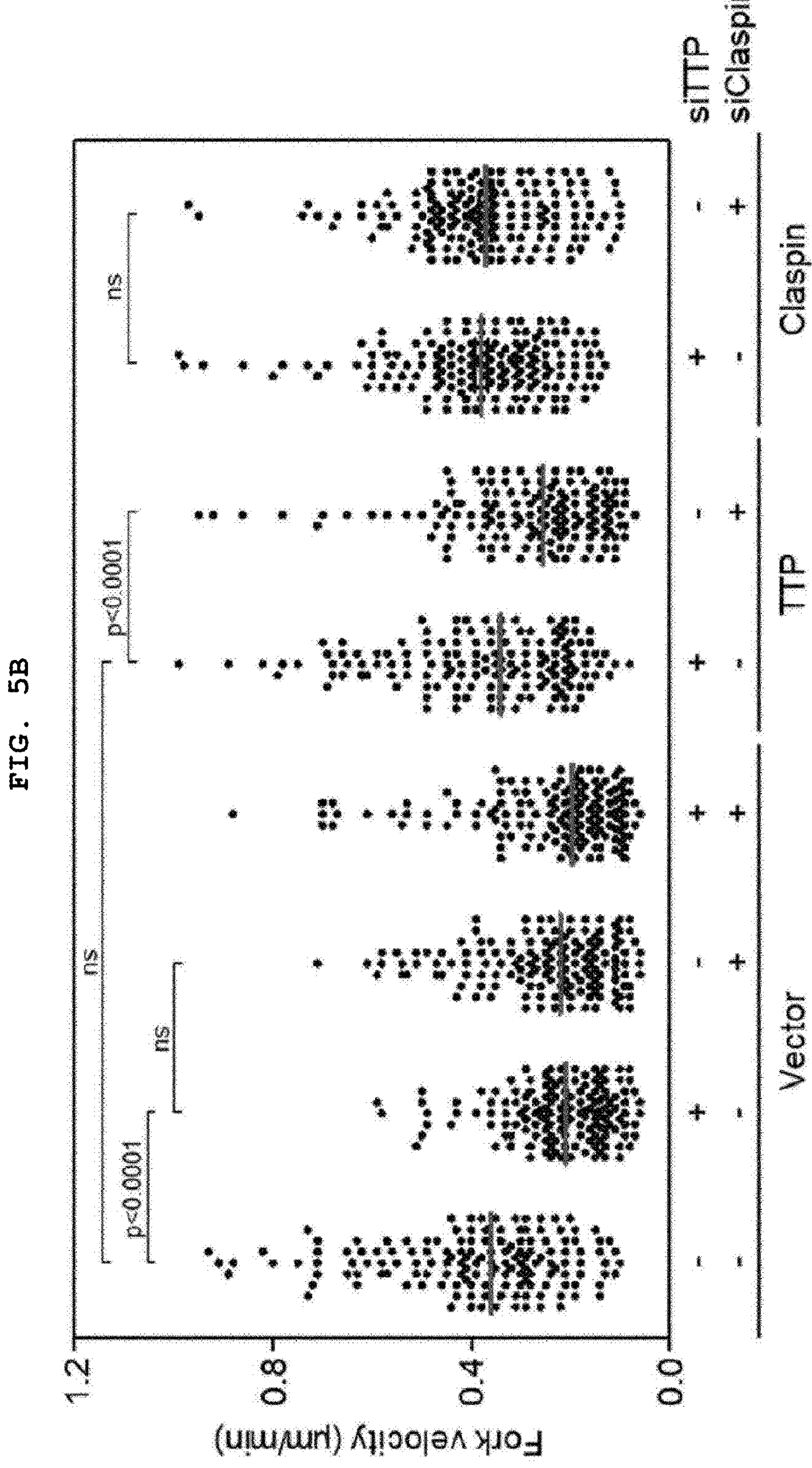

The DNA fiber analysis showed that the average fork velocity in control cells was 0.36 μm/min, whereas that in Claspin-deficient cells was 0.22 μm/min, meaning a substantial reduction, as reported previously. Intriguingly, depletion of TTP also led to reduction in fork velocity (0.21 μm/min), which is equivalent to the slowing seen in Claspin-deficient cells (FIG. 5B). When both Claspin and TTP were depleted at the same time, there was no further reduction. Thus, TTP and Claspin seem to operate through the same pathway that regulates replication fork velocity under unperturbed conditions. Re-expression of TTP successfully restored the fork velocity in TTP-deficient cells, making it almost indistinguishable from fork velocity in the control cells (0.34 μm/min).

Finally, TTP overexpression in Claspin knockdown cells did not improve the fork velocity, but Claspin overexpression in TTP knockdown cells resulted in the full recovery of fork velocity, which suggests that TTP regulates replication fork velocity in a Claspin dependent manner during the normal progression of DNA replication.

Example 5. Confirmation of the Role of TTP on DNA DSB and Chromosomal Abnormalities Aberrant DNA replication and the failure to restart stalled replication forks cause DNA breaks and promote genome instability. Evidence also suggests that loss of function of ATR-CHK1 pathway results in dysregulation of DNA replication and a greater number of chromosomal breaks. Given the roles of TTP in ATR-CHK1 pathway and normal DNA replication, we hypothesized that TTP depletion may induce fork breakage and hence chromosomal aberrations.

Figure 6B:
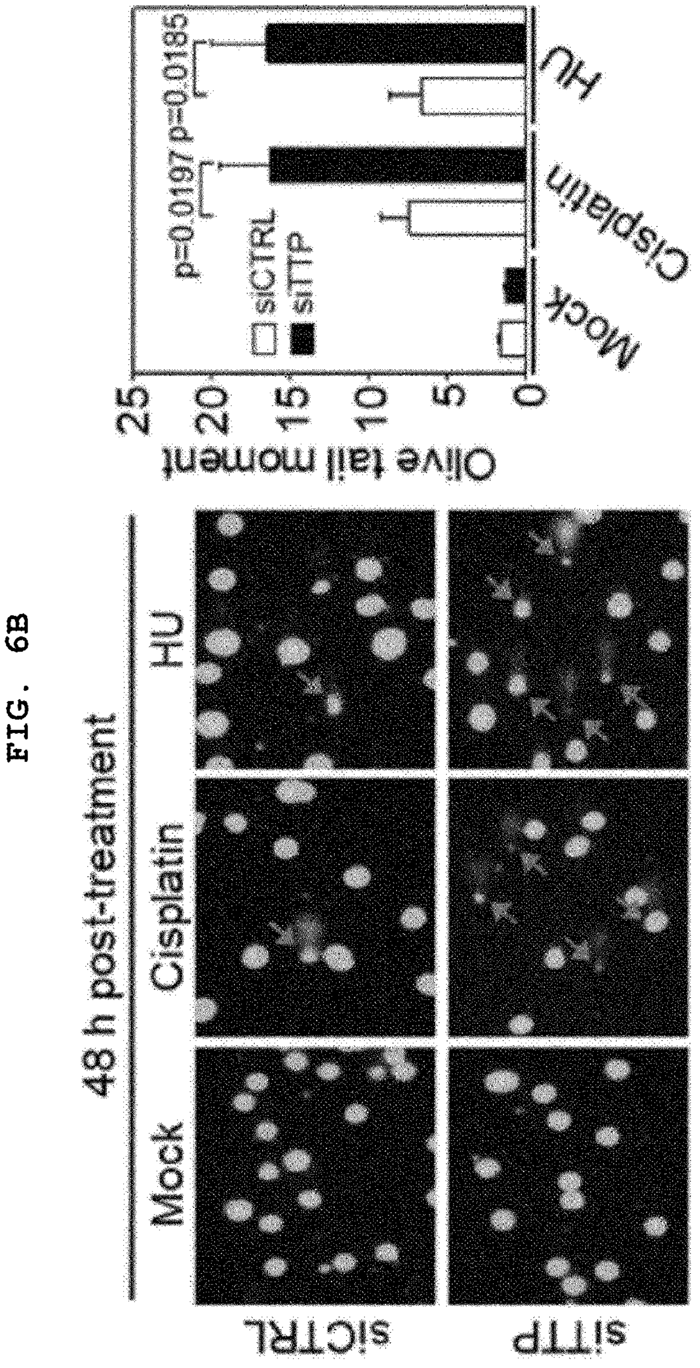

To assess this possibility, we determined the numbers of DNA DSBs under either HU- or cisplatin-induced replication stress. The coincidence of nuclear 53BP1 and γH2AX foci at the same cell was quantified as a surrogate of the DSB number after HU or cisplatin treatment. Compared to the mock depletion, TTP depletion yielded substantially more DSBs after cisplatin or HU treatment (FIG. 6A). Additionally, we observed around two-fold longer comet-like DNA tails, indicative of DNA fragmentation, in the TTP-deficient cells upon genotoxic stresses (FIG. 6B).

Figure 6C:
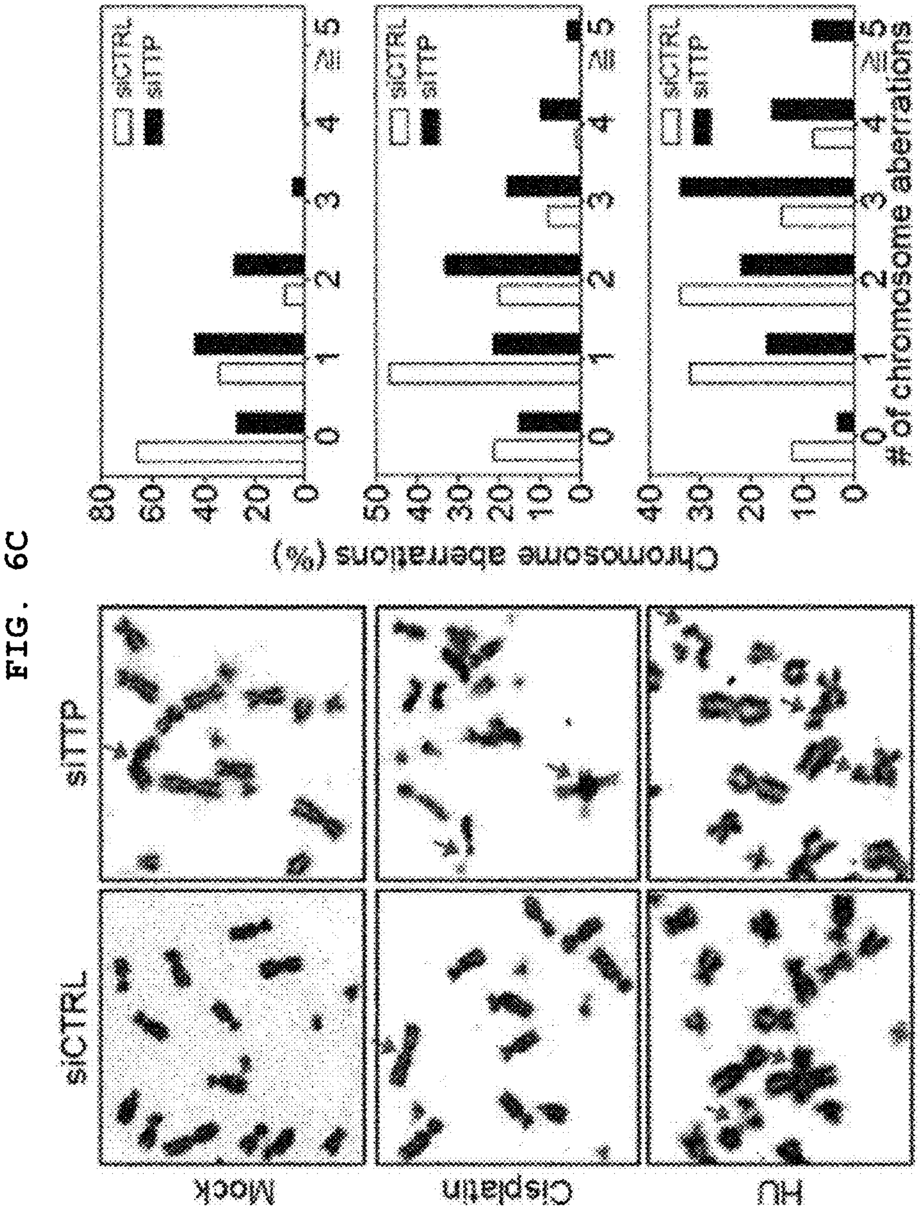

To evaluate the involvement of TTP for chromosome stability, we knocked TTP down and then measured the frequency of chromosomal aberrations in metaphase spreads with Giemsa staining. The results uncovered an approximately two-fold increase in the number of chromosomal aberrations per metaphase in TTP-deficient cells than control-deficient cells treated with either cisplatin or HU (FIG. 6C). Intriguingly, TTP depletion itself without genotoxic stress significantly increased the extent of chromosomal aberrations (FIG. 6C).

Figure 6D:
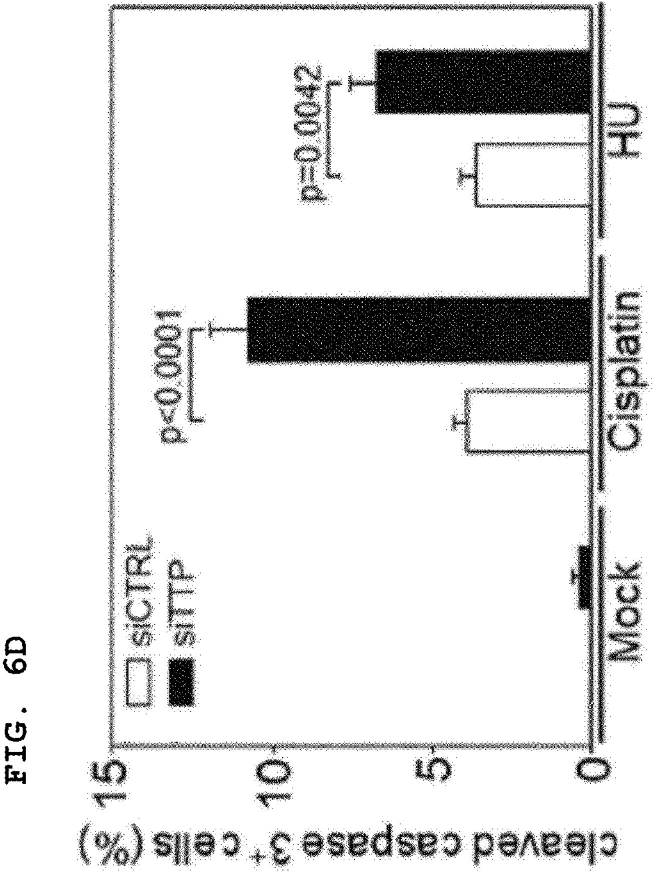
Figure 6D:
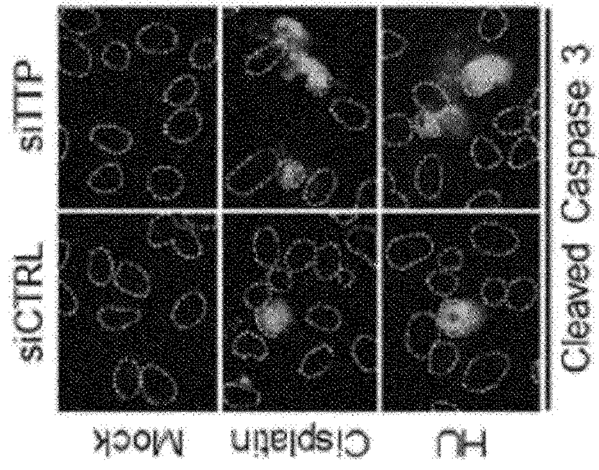

Furthermore, TTP depletion rendered cancer cells more susceptible to apoptosis that was measured by the cleaved caspase 3 analysis (FIG. 6D) and TUNEL assay (FIG. 6E) after either HU or cisplatin treatment. Based on these findings, we propose that TTP is required for the maintenance of the genome stability against replication stresses.

REFERENCE TO AN ELECTRONIC SEQUENCE LISTING

The contents of the electronic sequence listing (sequencelisting.xml; Size: 28,338 bytes; and Date of Creation: Oct. 13, 2022) is herein incorporated by reference in its entirety.

What is claimed is:

1. A method for enhancing sensitivity of DNA replication inhibitory anticancer-agent-resistant cancer cells, the method comprising contacting the cells with an anticancer adjuvant comprising a tristetraprolin inhibitor, wherein the tristetraprolin inhibitor is a siRNA (short interfering RNA) represented by SEQ ID NO: 1 or SEQ ID NO: 2;

wherein the DNA replication inhibitory anticancer-agent is cisplatin or hydroxyurea; and wherein the cancer is lung cancer or colorectal cancer.

2. The method of claim 1, wherein the adjuvant further comprises a DNA replication inhibitory anticancer agent.

* * * * *